(12) United States Patent
Ito et al.

(10) Patent No.: US 9,888,838 B2
(45) Date of Patent: Feb. 13, 2018

(54) LIGHT SOURCE DEVICE

(71) Applicant: OLYMPUS CORPORATION, Tokyo (JP)

(72) Inventors: Takeshi Ito, Hino (JP); Eiji Yamamoto, Hachioji (JP); Hiroyuki Kamee, Koganei (JP)

(73) Assignee: Olympus Corporation, Tokyo (JP)

( * ) Notice: Subject to any disclaimer, the term of this patent is extended or adjusted under 35 U.S.C. 154(b) by 103 days.

(21) Appl. No.: 14/820,003

(22) Filed: Aug. 6, 2015

(65) Prior Publication Data

US 2015/0335232 A1    Nov. 26, 2015

Related U.S. Application Data

(63) Continuation of application No. PCT/JP2014/051356, filed on Jan. 23, 2014.

(30) Foreign Application Priority Data

Feb. 7, 2013   (JP) .................................. 2013-022150

(51) Int. Cl.
   *G03B 15/02*   (2006.01)
   *A61B 1/07*    (2006.01)
   (Continued)

(52) U.S. Cl.
   CPC ............ *A61B 1/07* (2013.01); *A61B 1/00009* (2013.01); *A61B 1/00096* (2013.01); *A61B 1/04* (2013.01);
   (Continued)

(58) Field of Classification Search
   CPC .... G01J 2003/102; G01J 3/108; G02B 23/26; G02B 6/0008; H04N 5/2354
   See application file for complete search history.

(56) References Cited

U.S. PATENT DOCUMENTS

2002/0014595 A1* 2/2002 Sendai ............... A61B 1/00009
                                                       250/458.1
2006/0293556 A1* 12/2006 Garner ............... A61B 1/00009
                                                       600/101
(Continued)

FOREIGN PATENT DOCUMENTS

EP    2213222 A1    8/2010
EP    2 407 763 A2  1/2012
(Continued)

OTHER PUBLICATIONS

English translation of International Preliminary Report on Patentability dated Aug. 20, 2015 together with the Written Opinion, received in related International Application No. PCT/JP2014/051356.

(Continued)

*Primary Examiner* — Ali Alavi
(74) *Attorney, Agent, or Firm* — Scully, Scott, Murphy & Presser, P.C.

(57) ABSTRACT

A light source device to illuminate a target to be imaged by an imaging unit which includes N kinds of light detection elements which wavelength sensitivity regions are different each other includes a light source section, an insertion portion, an illumination light emitting portion and a light guide member. The light source section emits M kinds of narrow-band light which have different peak wavelengths, a difference between the peak wavelengths being equal to or more than an effective wavelength gap. The insertion portion is configured to be inserted into an internal space of an object. The illumination light emitting portion is provided in the insertion portion and which emits an illumination light. The light guide member guides the narrow-band light emitted from the light source section to the illumination light emitting portion.

38 Claims, 17 Drawing Sheets

(51) Int. Cl.
*F21V 8/00* (2006.01)
*G01J 3/10* (2006.01)
*A61B 1/04* (2006.01)
*G02B 23/26* (2006.01)
*A61B 1/06* (2006.01)
*A61B 1/00* (2006.01)
*H04N 5/235* (2006.01)
*H04N 5/225* (2006.01)

(52) U.S. Cl.
CPC ............ *A61B 1/063* (2013.01); *A61B 1/0638* (2013.01); *G01J 3/10* (2013.01); *G02B 6/0008* (2013.01); *G02B 23/26* (2013.01); *H04N 5/2256* (2013.01); *H04N 5/2354* (2013.01); *G01J 2003/104* (2013.01); *H04N 2005/2255* (2013.01)

(56) References Cited

U.S. PATENT DOCUMENTS

| | | | | |
|---|---|---|---|---|
| 2010/0194871 | A1* | 8/2010 | Komukai | A61B 1/00096 348/68 |
| 2011/0068278 | A1* | 3/2011 | Morishita | A61B 1/043 250/458.1 |
| 2011/0237883 | A1* | 9/2011 | Chun | A61B 1/0638 600/109 |
| 2011/0261353 | A1* | 10/2011 | Teramura | A61B 1/00096 356/213 |
| 2012/0302847 | A1* | 11/2012 | Ozawa | A61B 1/00009 600/339 |

FOREIGN PATENT DOCUMENTS

| | | |
|---|---|---|
| EP | 2526854 A1 | 11/2012 |
| JP | 10-286235 A | 10/1998 |
| JP | 2007275243 A | 10/2007 |
| JP | 2010-75513 A | 4/2010 |
| JP | 2010-172530 A | 8/2010 |
| JP | 2012-239816 A | 12/2012 |
| WO | 2011/113162 A1 | 9/2011 |
| WO | 2012/066553 A1 | 5/2012 |

OTHER PUBLICATIONS

Extended Supplementary European Search Report dated Oct. 10, 2016 in related European Patent Application No. 14 74 9503.0.
International Search Report dated Apr. 8, 2014 received in International Application No. PCT/JP2014/051356.
Chinese Office Action dated Jun. 13, 2016 in related Chinese Patent Application No. 201480007702.0.
Japanese Office Action dated Oct. 25, 2016 in related Japanese Patent Application No. 2013-022150.
Chinese Office Action dated Nov. 16, 2017 received in Chinese Patent Application No. 201480007702.0, together with an English-language translation.

* cited by examiner

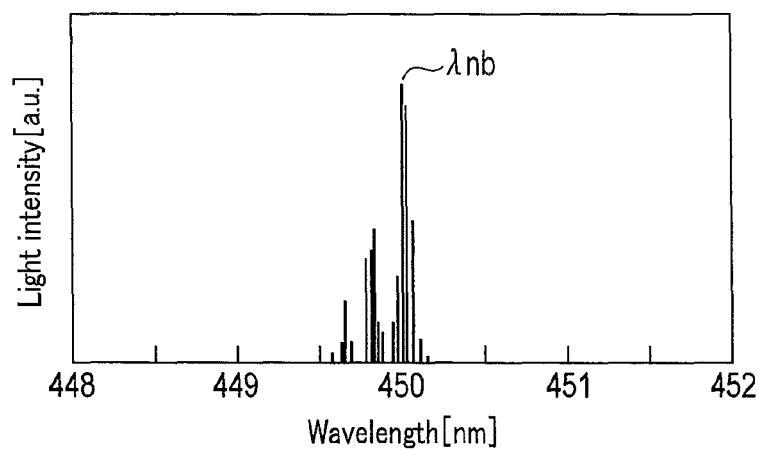
F I G. 2
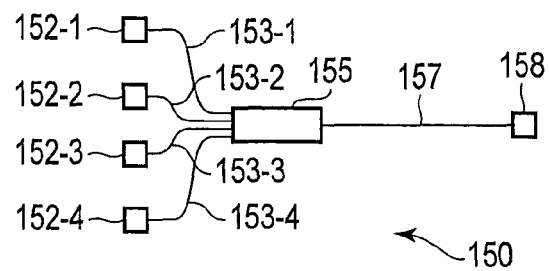
F I G. 3
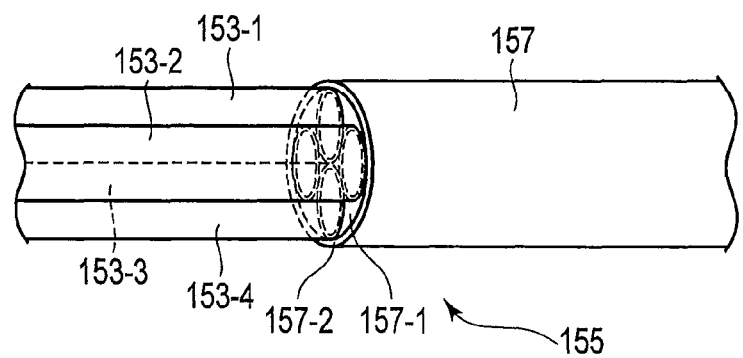
F I G. 4

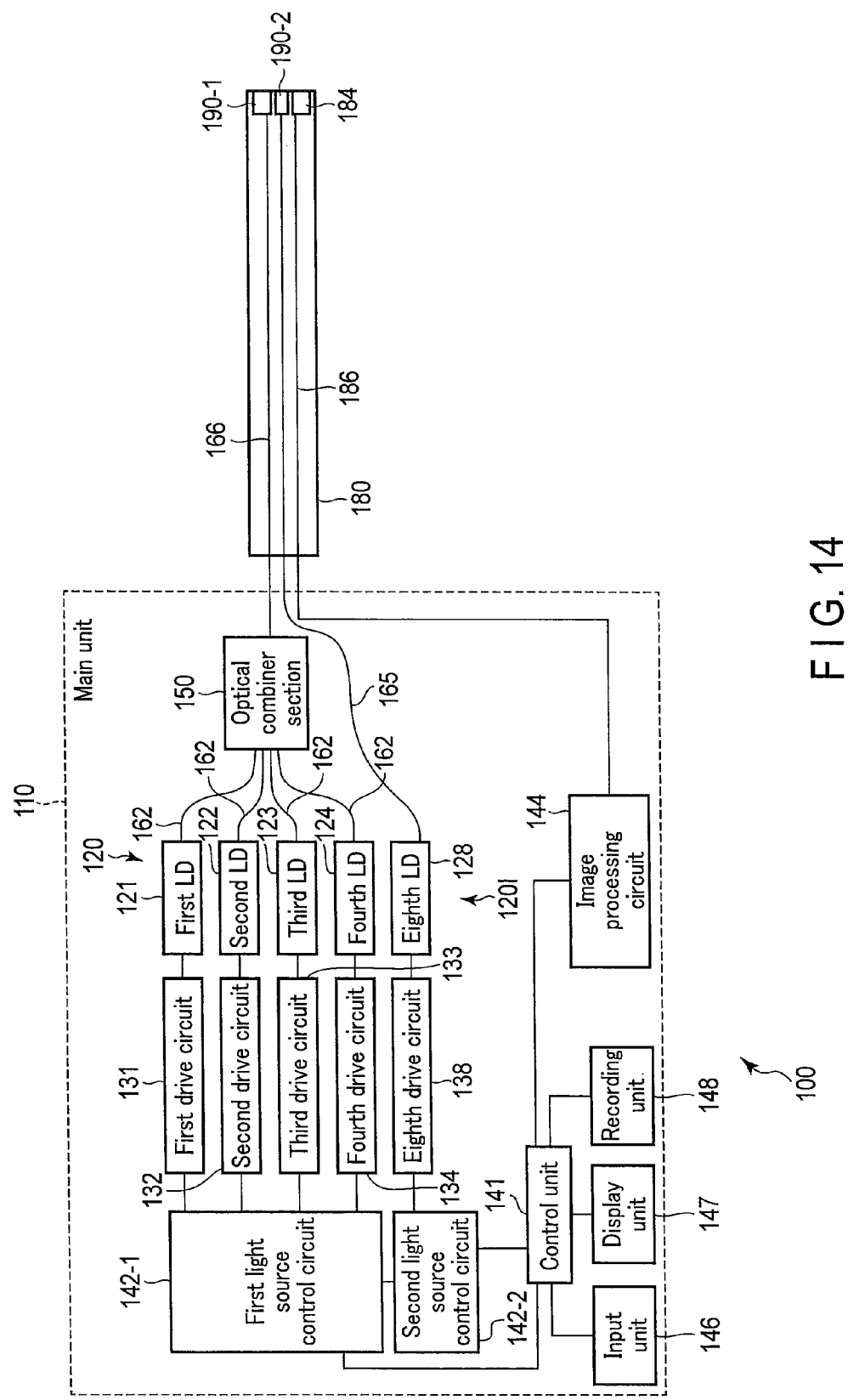
F I G. 14

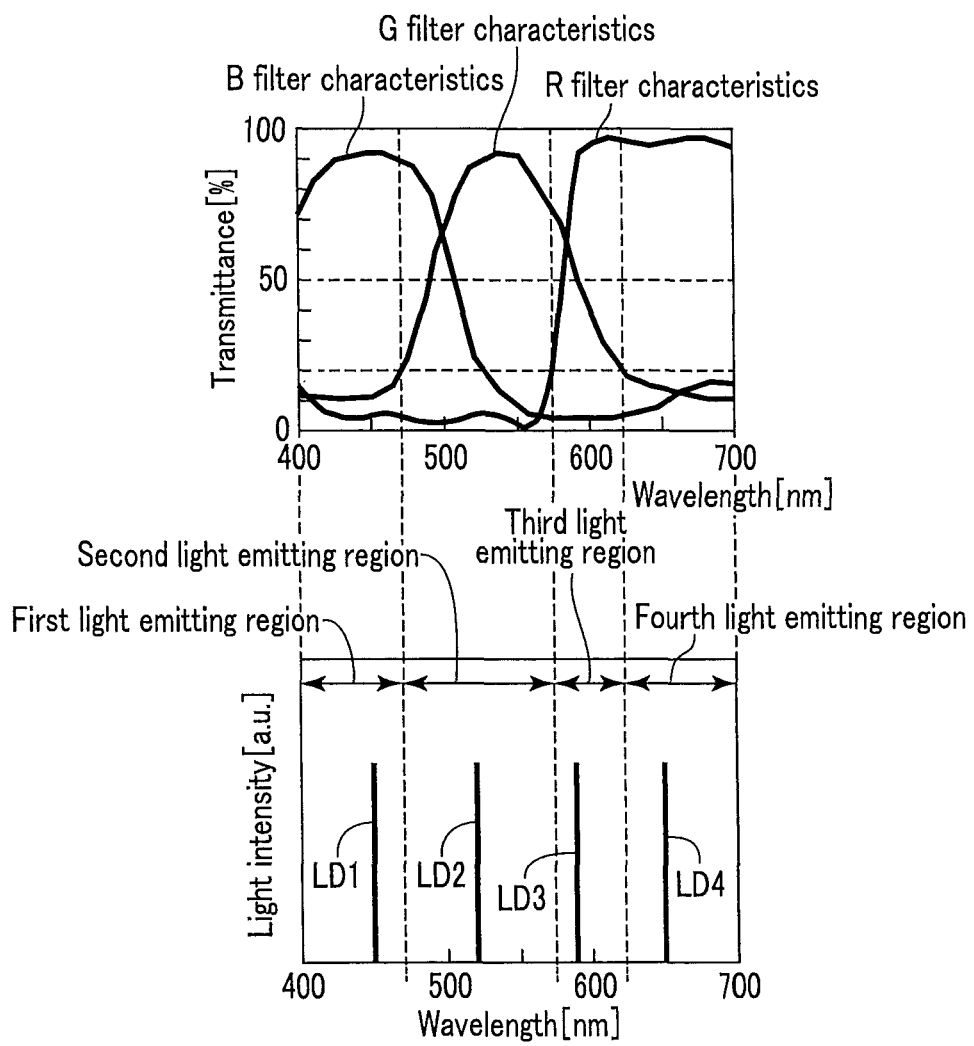
F I G. 16

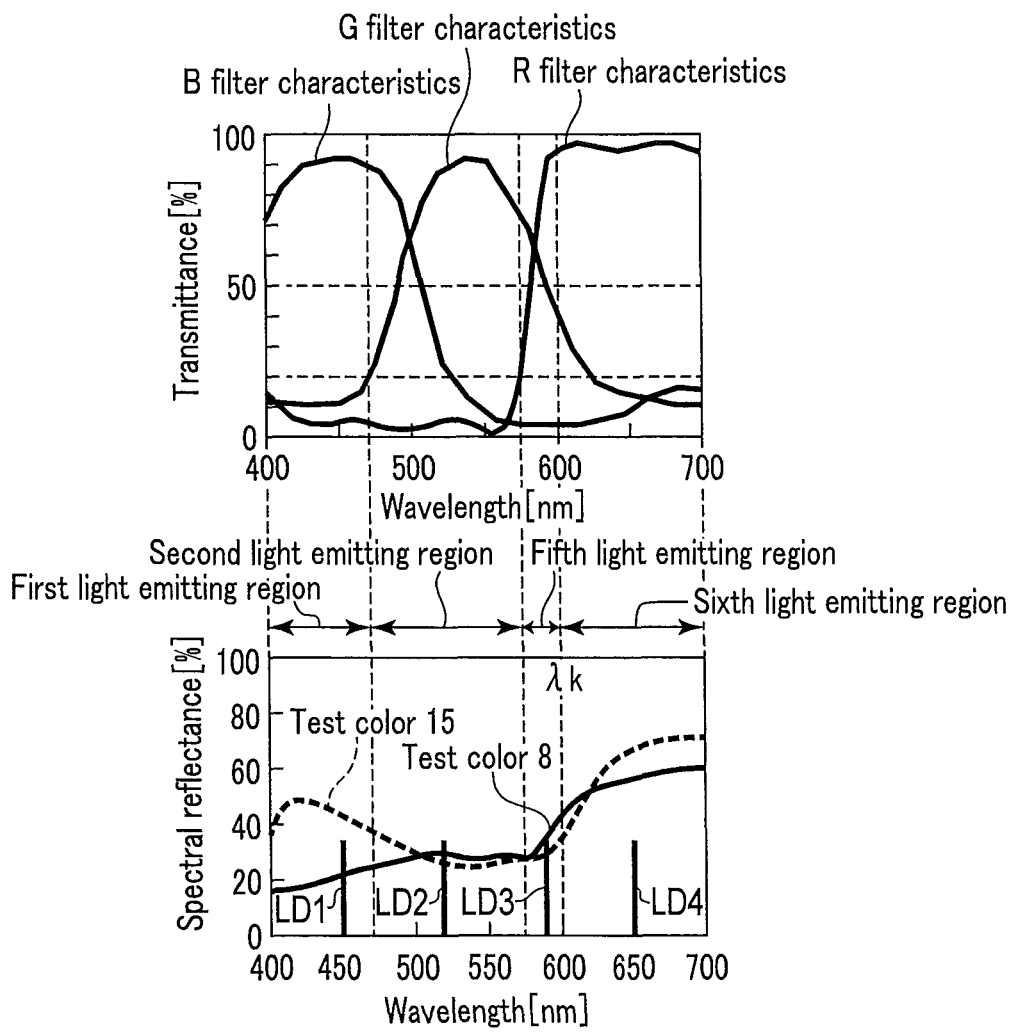
F I G. 17

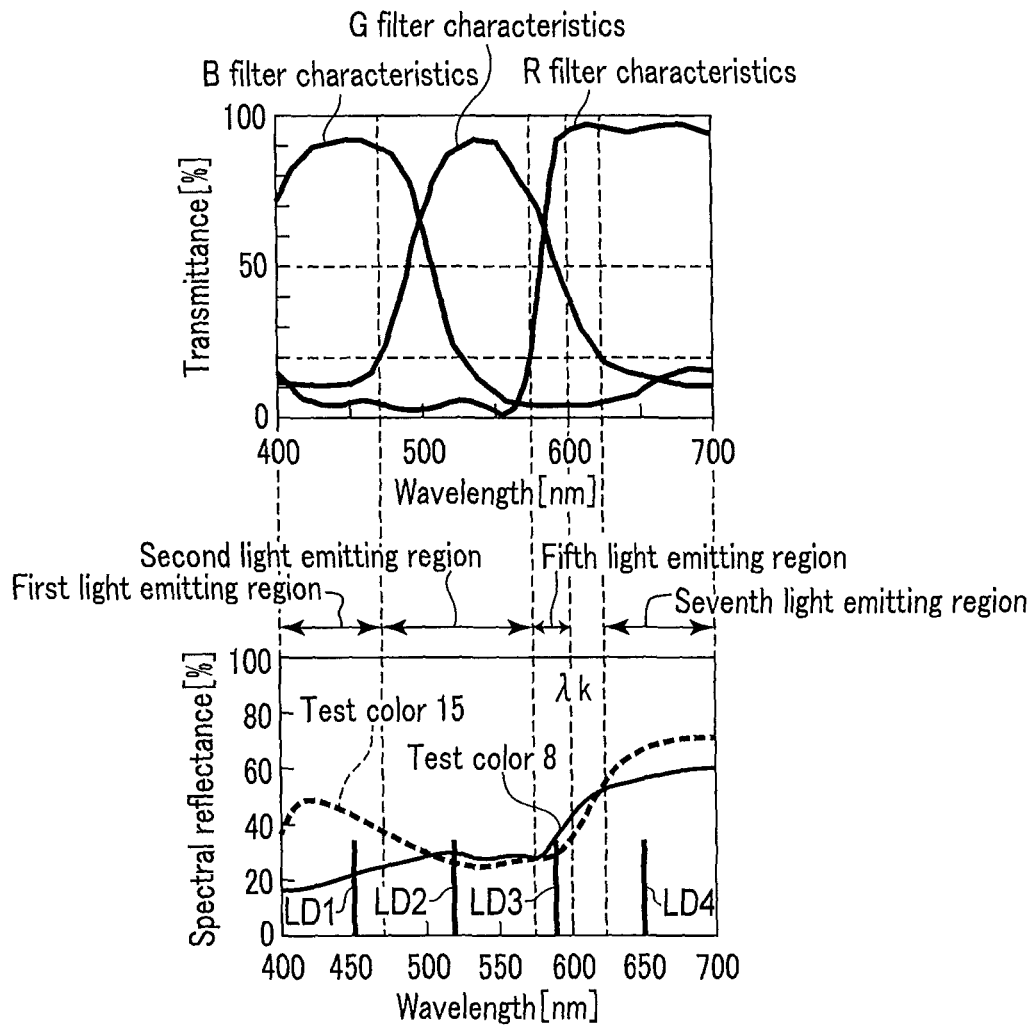
F I G. 18

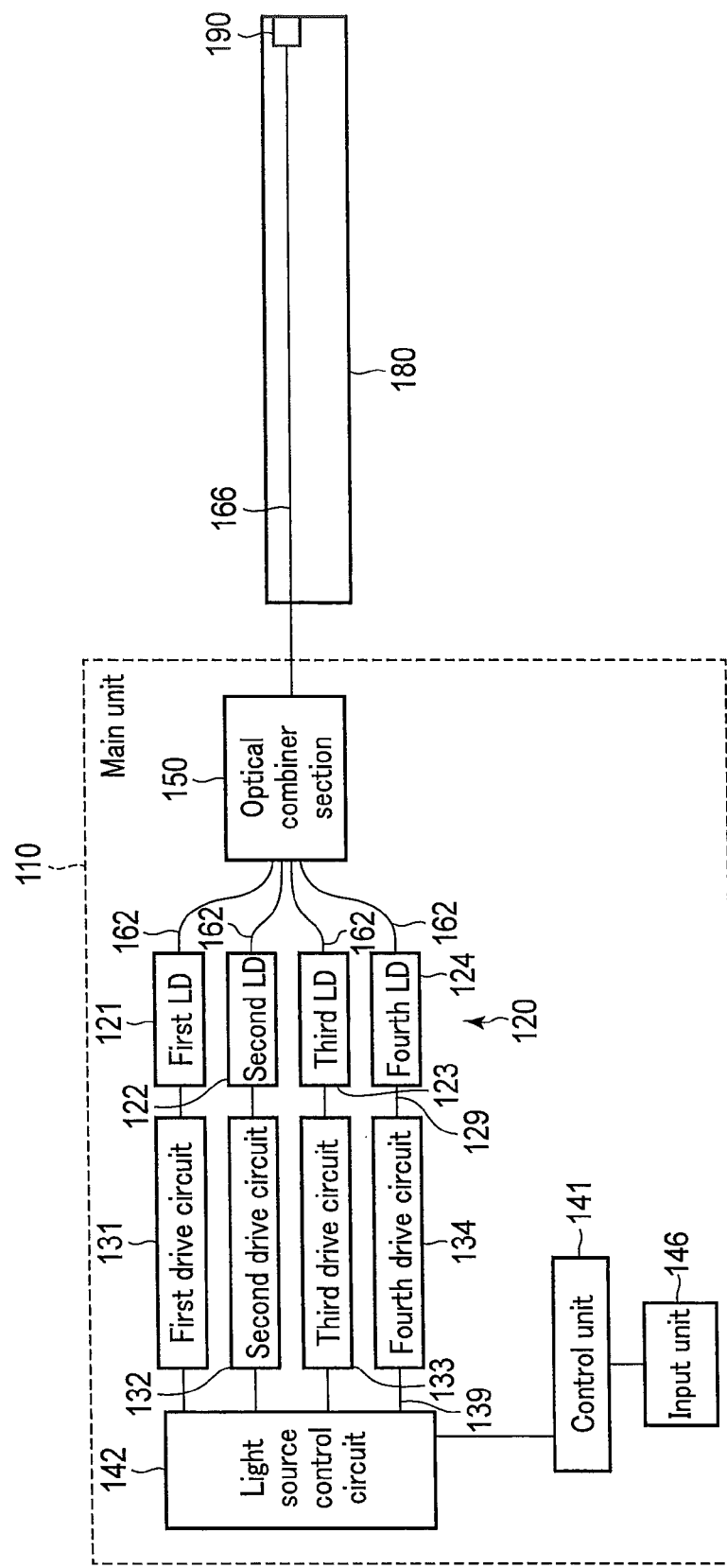
F I G. 19

LIGHT SOURCE DEVICE

CROSS-REFERENCE TO RELATED APPLICATIONS

This application is a Continuation Application of PCT Application No. PCT/JP2014/051356, filed Jan. 23, 2014 and based upon and claiming the benefit of priority from prior Japanese Patent Application No. 2013-022150, filed Feb. 7, 2013, the entire contents of all of which are incorporated herein by reference.

BACKGROUND OF THE INVENTION

1. Field of the Invention

The present invention relates to a light source device, and more particularly, it relates to a light source device which illuminates a target to be imaged by an imaging unit.

2. Description of the Related Art

A so-called fiber light source combining a small-size light source and an optical fiber has been generally known. Such a fiber light source is suited to illumination within a thin structure. As an example of the utilization of a light source device that uses such a fiber light source, Jpn. Pat. Appln. KOKAI Publication No. 10-286235 has disclosed an example of an endoscope equipped with a light source device combining a laser light source which emits three-color laser light of red (R), green (G) and blue (B), an optical fiber, a diffusion plate, and an illumination intensity distribution adjusting filter. Since the optical fiber highly efficiently guides the laser light, a highly efficient and bright light source device can be obtained by this combination of the laser light source and the optical fiber.

The light source device according to Jpn. Pat. Appln. KOKAI Publication No. 10-286235 uses an He—Cd laser light source which is a three-primary-color (white) laser light source for simultaneously emitting a blue laser light having a wavelength of 441.6 nm, a green laser light having a wavelength of 537.8 nm, and a red laser light having a wavelength of 636.0 nm, and an He—Ne laser light source for emitting a red laser light having a wavelength of 632.8 nm. The laser light emitted from these light sources are guided to the distal end of the endoscope by a light guide, and applied to a living body which is an illumination target via the diffusion plate and the illumination intensity distribution adjusting filter.

In general, when the diffused laser light is used as an illumination light, information regarding wavelengths that are not included in the laser light is absent. That is, it is known that when a laser light having a wavelength of 636.0 nm is used as red, red color reproducibility deteriorates if the reflectivity of red having a wavelength of 636.0 nm is considerably different from the reflectivity at other wavelengths. For example, an object which hardly reflects the light having a wavelength in the vicinity of 636.0 nm and which well reflects other light in the red region is observed. In this case, even if the object actually looks red, the object may look dark when a red laser light having a wavelength of 636.0 nm is applied to the object.

Thus, in Jpn. Pat. Appln. KOKAI Publication No. 10-286235, the red laser light source having a wavelength of 632.8 nm is used in addition to the red laser light source having a wavelength of 636.0 nm to improve the red color reproducibility. However, the wavelength difference of the laser light emitted by these light sources is only 3.2 nm. When the wavelength difference is small, not much improvement of color reproducibility can be expected.

BRIEF SUMMARY OF THE INVENTION

According to an aspect of the present invention, a light source device to illuminate a target to be imaged by an imaging unit which includes N (N is a natural number) kinds of light detection elements which wavelength sensitivity regions that are detectable wavelength bands are different each other includes a light source section configured to emit M (M is a natural number greater than N) kinds of narrow-band light which have different peak wavelengths, a difference between the peak wavelengths being equal to or more than an effective wavelength gap; an insertion portion configured to be inserted into an internal space of an object where the target exists; an illumination light emitting portion which is provided in the insertion portion and which emits an illumination light; and a light guide member which guides the narrow-band light emitted from the light source section to the illumination light emitting portion, the guided light being emitted from the illumination light emitting portion as the illumination light.

According to an aspect of the present invention, a light source device to illuminate a target to be imaged by an imaging unit which includes N (N is a natural number) kinds of light detection elements which wavelength sensitivity regions that are detectable wavelength bands are different each other includes a light source section which has K (K is a natural number greater than N) light emitting regions having different wavelength ranges and which emits a plurality of kinds of narrow-band light so that a peak wavelength of at least one kind of narrow-band light is included in each of the light emitting regions; an insertion portion configured to be inserted into an internal space of an object where the target exists; an illumination light emitting portion which is provided in the insertion portion and which emits an illumination light; and a light guide member which guides the narrow-band light emitted from the light source section to the illumination light emitting portion, the guided light being emitted from the illumination light emitting portion as the illumination light.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a graph showing an example of wavelength characteristics of a semiconductor laser light source;

FIG. 3 is a diagram showing an overview of a configuration example of an optical combiner section of the light source imaging apparatus according to the first embodiment;

FIG. 4 is a diagram showing an overview of the configuration example of the optical combiner section of the light source imaging apparatus according to the first embodiment;

FIG. 14 is a block diagram showing an overview of a configuration example of a light source imaging apparatus according to a first modification of the third embodiment;

FIG. 16 is a graph showing an example of wavelength characteristics associated with a light source imaging apparatus according to a fourth embodiment;

FIG. 17 is a graph showing an example of wavelength characteristics associated with a light source imaging apparatus according to a modification of the fourth embodiment;

FIG. 18 is a graph showing an example of wavelength characteristics associated with the light source imaging apparatus according to the modification of the fourth embodiment; and FIG. 19 is a block diagram showing an overview of a configuration example of a light source apparatus according to the modification of each of the embodiments.

DETAILED DESCRIPTION OF THE INVENTION

First Embodiment

Figure 1:
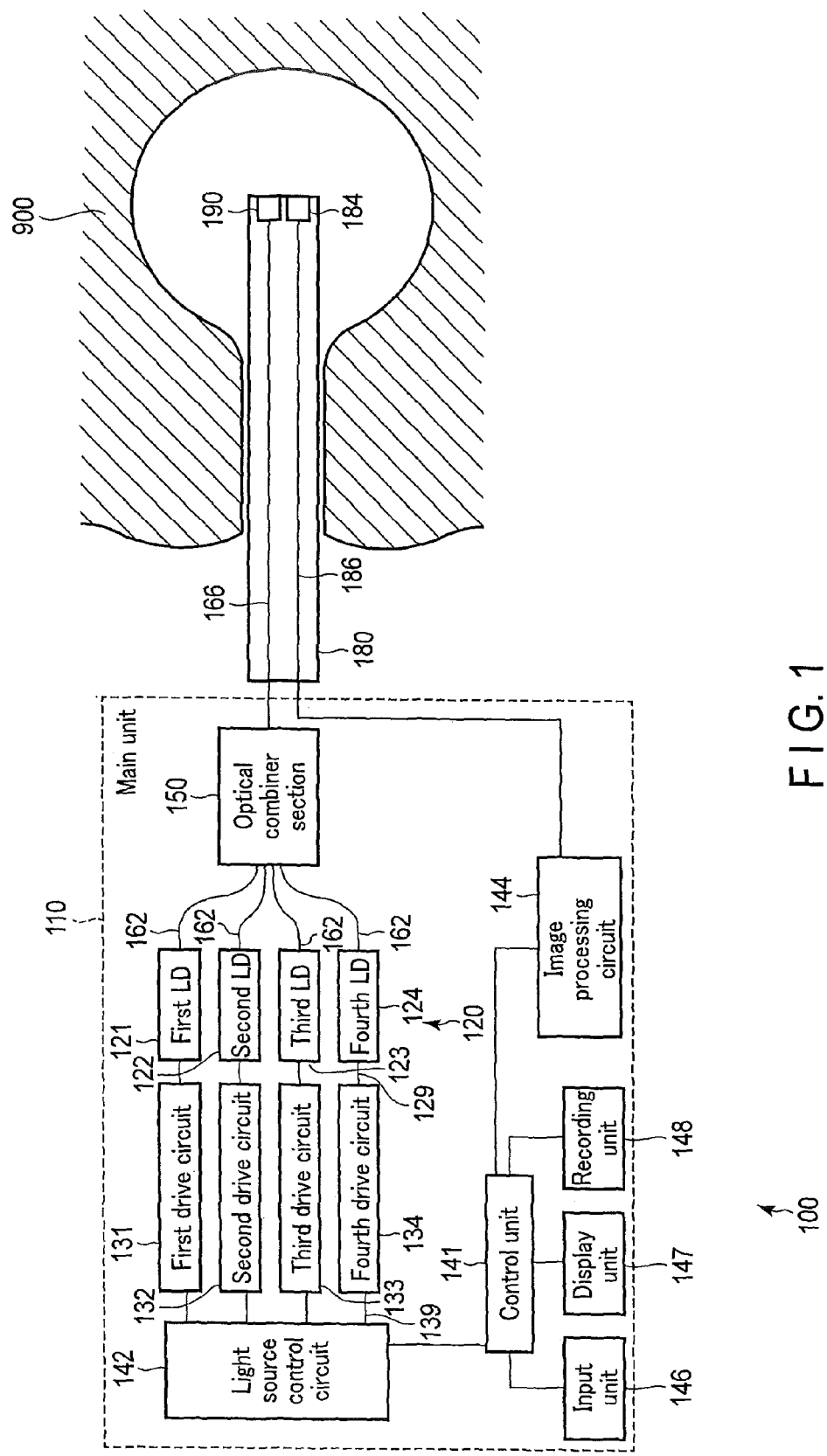
FIG. 1 is a block diagram showing an overview of a configuration example of a light source imaging apparatus according to a first embodiment.

A first embodiment of the present invention is described with reference to the drawings. The present embodiment relates to a light source imaging apparatus 100 including a light source device, and an imaging device for imaging an observation target illuminated by the light source device. An overview of a configuration example of the light source imaging apparatus 100 according to the present embodiment is shown in FIG. 1. As shown in FIG. 1, the light source imaging apparatus 100 comprises a main unit 110 and an insertion portion 180.

The main unit 110 is provided with a light source section 120 including a first semiconductor laser light source (LD) 121, a second semiconductor laser light source (LD) 122, a third semiconductor laser light source (LD) 123, and a fourth semiconductor laser light source (LD) 124. These four semiconductor laser light sources are different in the wavelengths of emitted light. The main unit 110 is provided with a first drive circuit 131 for driving the first semiconductor laser light source 121, a second drive circuit 132 for driving the second semiconductor laser light source 122, a third drive circuit 133 for driving the third semiconductor laser light source 123, and a fourth drive circuit 134 for driving the fourth semiconductor laser light source 124. The first to fourth drive circuits and the first to fourth semiconductor laser light sources are connected by electric wiring lines 129, respectively.

The main unit 110 further has a control unit 141, a light source control circuit 142, an image processing circuit 144, an input unit 146, a display unit 147, a recording unit 148, and an optical combiner section 150. The control unit 141 is respectively connected to the light source control circuit 142, the image processing circuit 144, the input unit 146, the display unit 147, and the recording unit 148, and controls the operation of each section.

The light source control circuit 142 and the first to fourth drive circuits are connected to each other via control signal lines 139. The light source control circuit 142 controls the turning on and off of each of the first to fourth semiconductor laser light sources, and the intensity of a laser light emitted from each of the first to fourth semiconductor laser light sources. The laser light emitted from the first to fourth semiconductor laser light sources is guided to the optical combiner section 150 by entrance side optical fibers 162, respectively. The optical combiner section 150 mixes the guided laser light, and then causes the mixed light to enter one exit side optical fiber 166.

The insertion portion 180 has an elongated shape, and has one end connected to the main unit 110. One end connected to the main unit 110 is referred to as a proximal side, and the other end is referred to as a distal side. A light emitting portion 190 and an imaging unit 184 are provided at the distal end of the insertion portion 180. The insertion portion 180 is provided with the exit side optical fiber 166 which guides, to the light emitting portion 190, the laser light emitted from the first to fourth semiconductor laser light sources and mixed by the optical combiner section 150. The light based on the laser light guided by the exit side optical fiber 166 emits from the light emitting portion 190. Although the light emitting portion 190 is provided in the distal face of the insertion portion 180 in the case shown in FIG. 1, the light emitting portion 190 may be provided in the circumferential surface of the insertion portion 180.

The imaging unit 184 includes an image sensor. The imaging unit 184 images a region illuminated by the light emitted from the light emitting portion 190, and acquires image information. The imaging unit 184 is connected to the image processing circuit 144 in the main unit 110 by an image signal line 186. The imaging unit 184 outputs the obtained image information to the image processing circuit 144. The image processing circuit 144 subjects the image information acquired in the imaging unit 184 to image processing. The image processing circuit 144 outputs the processed image information to the control unit 141.

The input unit 146 includes general input means such as a button, a dial, a slider, a keyboard, or a mouse, and acquires an instruction from a user. The input unit 146 outputs the acquired information to the control unit 141. The display unit 147 includes a general display device such as a liquid crystal monitor, and displays images processed in the image processing circuit 144, and various kinds of control information. The recording unit 148 includes a general recording medium, and records, for example, images processed in the image processing circuit 144.

Although the control signal lines 139, the electric wiring lines 129, and the image signal line 186 are each shown by one straight line in FIG. 1, it should be understood that each of the lines may have more than one line. Moreover, in FIG. 1, components that are naturally required such as a power cable are not shown.

The insertion portion 180 has an elongated and substantially circular cylindrical appearance, and has a shape that is easily inserted into an internal space of the observation target. In other words, the insertion portion 180 has a shape that easily illuminates the internal space of the observation target having a narrow entrance which is difficult to illuminate with a general light source device. For example, as shown in FIG. 1, an internal space of an observation target 900 can be a space slightly expanding to the far side from a narrow entrance. It is difficult for an external light such as interior illumination and sunlight to come into such a space. In particular, when the insertion portion 180 is inserted, the narrow entrance is further blocked by the insertion portion 180, and almost no external light comes in. That is, most of the illumination light in the internal space is the light emitted from the light emitting portion 190, and compared to this light, the external light is almost negligible. The light source imaging apparatus 100 according to the present embodiment is suited to illuminating in a space in which external light is almost negligible compared to the illumination light.

The first to fourth semiconductor laser light sources (LD) are described in detail. The semiconductor laser light sources are solid-state light source devices which emit laser light when an electric current is supplied to semiconductor elements. Semiconductor laser light sources that are generally in practical use emit various wavelengths from ultraviolet light to infrared light. The semiconductor laser light sources have advantages such as a small size and low power consumption. Active development of the semiconductor laser light sources is carried out for, for example, higher intensity of light and diversification of wavelengths.

In general, laser light is light having wavelength characteristics of a line spectrum with an extremely small wavelength width. In the case of a semiconductor laser, the width of a spectral line (spectral band width) is generally several nm or less. Semiconductor laser light sources include, for example, an edge emitting type (stripe laser) which emits light from a cleavage plane of a wafer, and a surface emitting type (vertical cavity surface emitting, laser; VCSEL) which emits light from the surface of a wafer. Also in practical use is a composite semiconductor laser light source typified by a second harmonic type (SHG semiconductor laser) in which a nonlinear crystal is combined with a semiconductor laser emitting portion to shorten an oscillation wavelength by half.

In the present embodiment, four semiconductor laser light sources shown below are used. That is, the first semiconductor laser light source 121 is a multimode semiconductor laser light source which emits a blue laser light having a wavelength of 450 nm. The second semiconductor laser light source 122 is a multimode semiconductor laser light source which emits a blue-green laser light having a wavelength of 520 nm. The third semiconductor laser light source 123 is a multimode SHG semiconductor laser light source which emits an orange laser light having a wavelength of 590 nm. The fourth semiconductor laser light source 124 is a multimode semiconductor laser light source which emits a red laser light having a wavelength of 650 nm.

Each of the semiconductor laser light sources is a multimode laser. For example, as shown in FIG. 2, the multimode semiconductor laser light source emits laser light having more than one wavelength, and their wavelengths are included in a wavelength range of about several nm from the shortest wavelength to the longest wavelength. FIG. 2 shows an example of a light emission spectrum of the multimode semiconductor laser light source which emits light having a wavelength of 450 nm. This light emission spectrum has tens of line spectrum components, and the intensity ratio of each line spectrum and the number of line spectra change with time. The width of the wavelength region of the light emission spectrum has an expansion of about 1 nm. When the multimode laser light having such a spectrum is used as a narrow-band light, a peak wavelength $\lambda nb$ as the narrow-band light is defined as a wavelength having the highest light intensity in the present embodiment. In the present embodiment, a peak wavelength $\lambda nb1$ of the first semiconductor laser light source 121 is 450 nm. Similarly, a peak wavelength $\lambda nb2$ of the second semiconductor laser light source 122 is 520 nm, a peak wavelength $\lambda nb3$ of the third semiconductor laser light source 123 is 590 nm, and a peak wavelength $\lambda nb4$ of the fourth semiconductor laser light source 124 is 650 nm.

In the present embodiment, the regions which are located between the laser light spectrum of the first semiconductor laser light source 121 and the laser light spectrum of the second semiconductor laser light source 122, between the laser light spectrum of the second semiconductor laser light source 122 and the laser light spectrum of the third semiconductor laser light source 123, and between the laser light spectrum of the third semiconductor laser light source 123 and the laser light spectrum of the fourth semiconductor laser light source 124 and which include no laser light are defined as wavelength lacking regions. In the present embodiment, a width of 1 nm or less of the spectral component in each laser light is in a negligible range compared to a width of several ten nm which is the width of the wavelength lacking region. Therefore, the distance between the peak wavelengths can be considered as the width of the wavelength lacking region. In the present embodiment, the width of the wavelength lacking region between the first semiconductor laser light source 121 and the second semiconductor laser light source 122 is 70 nm, the width of the wavelength lacking region between the second semiconductor laser light source 122 and the third semiconductor laser light source 123 is 70 nm, and the width of the wavelength lacking region between the third semiconductor laser light source 123 and the fourth semiconductor laser light source 124 is 60 nm.

The width of the wavelength lacking region according to the present embodiment is about 30 to 40 nm smaller than that in the above-mentioned case according to Jpn. Pat. Appln. KOKAI Publication No. 10-286235. That is, although four laser light sources are used both in the present embodiment and in Jpn. Pat. Appln. KOKAI Publication No. 10-286235, a narrower wavelength lacking region is set in the present embodiment.

The first to fourth drive circuits are described in detail. The first to fourth drive circuits apply proper electric currents to the first to fourth semiconductor laser light sources. The first to fourth drive circuits adjust the electric currents applied to the first to fourth semiconductor laser light sources in accordance with a control signal input from the light source control circuit 142 via the control signal lines 139. The first to fourth drive circuits control the lighting states of the first to fourth semiconductor laser light sources; for example, turn on or off or pulse-light the first to fourth semiconductor laser light sources. The first to fourth drive circuits have functions to prevent electrical malfunction of the first to fourth semiconductor laser light sources due to a rapid electric current increase or application of a nonstandard electric current or voltage. Moreover, the first to fourth drive circuits have various functions of general semiconductor laser drive circuits.

The light source control circuit 142 is described in detail. The light source control circuit 142 has a function to control the first to fourth semiconductor laser light sources in relation to one another, and also independently control the first to fourth semiconductor laser light sources. For example, when the first to fourth semiconductor laser light sources are combined, mixing of light emitted from the laser light sources with substantially equal intensity results in a substantially white light. When the color of the illumination light needs to be adjusted for the purpose of illumination, the mixed light can be illumination light of various colors by properly adjusting the light intensity ratio of the first to fourth semiconductor laser light sources. The light source control circuit 142 can simultaneously increase or decrease the intensity of the entire laser light while maintaining a constant light intensity ratio of the laser light derived from the four first to fourth semiconductor laser light sources. The light source control circuit 142 can also independently increase or decrease the intensity of a particular laser light alone, and turns on/off the particular laser light.

When, for example, the light intensity increases or decreases while a constant light intensity ratio of the first to fourth semiconductor laser light sources is maintained under the control of the light source control circuit 142, the color of the illumination light does not change, and the brightness of the illumination light only increases or decreases. When the intensity of the first to fourth semiconductor laser light sources is independently adjusted, the color of the illumination light is variously adjusted. Moreover, when all the first to fourth semiconductor laser light sources simultaneously turn on and off, the illumination light turns on and off in a desired color. When the laser light sources sequentially turn on and off at different timings, the color of the illumination light sequentially changes. The light source control circuit 142 can be configured to be capable of controlling the first to fourth semiconductor laser light sources for various other purposes.

The optical fibers are described in detail. In the present embodiment, the optical fibers are used to guide laser light to the optical combiner section 150 from the first to fourth semiconductor laser light sources and to guide light to the light emitting portion 190 from the optical combiner section 150. Various optical fibers that are in practical use are available as the optical fibers.

In the present embodiment, the multimode semiconductor laser light sources are used as the light sources. Thus, the multimode type optical fibers are used for efficient entering and guiding of the multimode laser light. General multimode type optical fibers have a core diameter of several ten to about 200 µm. The core diameter of the optical fiber is preferably large to improve the entrance rate of the laser light emitted from the semiconductor laser light source, and is preferably small for the ease of bending and diametrical reduction of the insertion portion 180. Therefore, the optical fibers to be used are selected based on, for example, the spreads of the laser light emitted from the light sources, the optical structure of a connecting portion for optically connecting the light sources and the optical fibers, the size of the insertion portion 180, and optical input/output requirements of the optical combiner section 150.

In the present embodiment, an optical fiber having a core diameter of about 50 µm and a cladding diameter of about 125 µm is used as the exit side optical fiber for guiding the laser light from the optical combiner section 150 provided in the main unit 110 to the light emitting portion 190 provided in the insertion portion 180. Not only optical fibers that are different in core diameter but also optical fibers having various characteristics are in practical use for each purpose. For example, optical fibers are selected suitably for purposes in accordance with the degree of a numerical aperture NA based on a refractive index difference between a core and a cladding, or a cladding diameter and a covering structure of the outside of the cladding that affect the ease of bending and strength.

Optical fibers of various materials are available. It is also possible to use not only conventionally used optical fibers with glass cores/glass claddings but also optical fibers with plastic cores/plastic claddings that are in widespread use for short distance light transmission. For a greater refractive index difference between a core and a cladding, a compound optical fiber in which a glass core and a plastic cladding are combined can also be used. In the present embodiment, optical fibers having quartz cores and glass claddings that are relatively high in optical durability are selected based on the intensities and wavelengths of the light to be used.

The optical combiner section 150 is described in detail. The optical combiner section 150 includes an optical element having a function to mix light entering from multiple entrance ends into light to be emitted from one exit end. That is, an optical element capable of coupling laser light which have been emitted from the light sources and guided by the corresponding optical fibers to one optical fiber can be used as the optical combiner section 150. For example, a prism type optical element in which a cross prism or a dichroic mirror are combined, or an optical fiber type optical element in which core portions of diametrically small optical fibers are connected to a core portion of one diametrically large optical fiber can be used as the optical combiner section 150.

An overview of one example of the optical fiber type optical combiner section 150 is shown in FIG. 3. As shown in this drawing, the optical combiner section 150 includes an optical combiner 155 having a function to mix light. Connected to the optical combiner 155 are one end of a first entrance side connection optical fiber 153-1, one end of a second entrance side connection optical fiber 153-2, one end of a third entrance side connection optical fiber 153-3, and one end of a fourth entrance side connection optical fiber 153-4. A first connector 152-1 to which the entrance side optical fiber 162 for the first semiconductor laser light source 121 is connected is provided at the other end of the first entrance side connection optical fiber 153-1. A second connector 152-2 to which the entrance side optical fiber 162 for the second semiconductor laser light source 122 is connected is provided at the other end of the second entrance side connection optical fiber 153-2. A third connector 152-3 to which the entrance side optical fiber 162 for the third semiconductor laser light source 123 is connected is provided at the other end of the third entrance side connection optical fiber 153-3. A fourth connector 152-4 to which the entrance side optical fiber 162 for the fourth semiconductor laser light source 124 is connected is provided at the other end of the fourth entrance side connection optical fiber 153-4. One end of an exit side connection optical fiber 157 is connected to the optical combiner 155. An exit side connector 158 to which the exit side optical fiber 166 is connected is provided at the other end of the exit side connection optical fiber 157.

A connecting portion of the optical combiner 155 is shown in FIG. 4. FIG. 4 shows an example of the 4-in-1-out (four entrance ends and one exit end) optical combiner 155. Each of the end faces of the first entrance side connection optical fiber 153-1, the second entrance side connection optical fiber 153-2, the third entrance side connection optical fiber 153-3, and the fourth entrance side connection optical fiber 153-4 is pressed on the end face of a core 157-1 surrounded by a cladding 157-2 of the exit side connection optical fiber 157. The first to fourth entrance side connection optical fibers are optically connected to the exit side connection optical fiber 157. Although FIG. 4 is a schematic diagram for clarity, the part located in the vicinity of the connecting portion is actually fusion-bonded or fixed by, for example, an adhesive agent, and the connecting portion is entirely covered with a cover for improvement in mechanical strength.

The optical combiner 155 shown in FIG. 4 is configured so that the diameter of the exit side connection optical fiber 157 is larger than the diameter of each of the first to fourth entrance side connection optical fibers. Thus, there may be a diametrical difference between the entrance side and the exit side. The exit side connection optical fiber 157 may be gently tapered, and the exit side connection optical fiber 157 may be processed to be gradually thinner in the light traveling direction.

Although the example of the 4-in-1-out optical combiner section 150 is shown here, the present invention is not limited to this. A 2-in-1-out optical combiner and a multiple-in-1-out optical combiner in which a large number of input side optical fibers are coupled to one optical fiber have been in practical use, and various such optical combiners can be used. It is possible to adjust the number of entrance ends according to the purpose by connecting optical combiners in series. For example, it is possible to configure a 3-in-1-out optical combiner as a whole by connecting, to the entrance end of one 2-in-1-out optical combiner, the exit end of another 2-in-1-out optical combiner. It is also possible to configure optical combiners of various types by connecting various optical combiners in series or in parallel. It is to be noted that an optical combiner, when generally referred to, means the optical combiner 155 or means the whole optical combiner section 150.

The light emitting portion 190 is described in detail. The light emitting portion 190 emits, as illumination light, the laser light guided by the exit side optical fiber 166. The laser light includes four kinds of narrow-band light different in wavelength which have been emitted from the first to fourth semiconductor laser light sources and guided to the exit side optical fiber 166 by the optical combiner section 150. The light emitting portion 190 adjusts, according to an illumination purpose, the optical characteristics of the laser light which is primary light emitted from the first to fourth semiconductor laser light sources, and emits the laser light as illumination light.

The laser light may be dangerous to the human body depending on its radiation angle or on the light intensity per section angle. Thus, the light emitting portion 190 increases the radiation angle of the light to be emitted to a safe degree or increases the size of a light emitting point. Because of the degree of coherence length which is an optical characteristic of the laser light, that is, because of the high coherency, random luminescent spots known as speckle noise occur when the laser light is applied to, for example, a scattering surface. This speckle noise not only causes discomfort such as a flickering sensation to an observer but also becomes the cause of inhibiting the observation of details of an observation target. Thus, the light emitting portion 190 decreases the coherency of the laser light. Moreover, the NA, which is an index based on the refractive index difference between the core and the cladding of the optical fiber, has wavelength dependence as the refractive index. The radiation angle of the laser light emitted from the exit end of the optical fiber depends on the NA. Thus, the radiation angle of the laser light emitted from the exit end of the optical fiber has wavelength dependence. Here, if the radiation angle varies according to wavelength, concentric color unevenness occurs in the light emitted from the optical fiber. As a result, the color appears different depending on the position of the illumination target. Therefore, to eliminate the variation of the radiation angle according to wavelength, the light emitting portion 190 adjusts the radiation angle and a light distribution.

Figure 5:
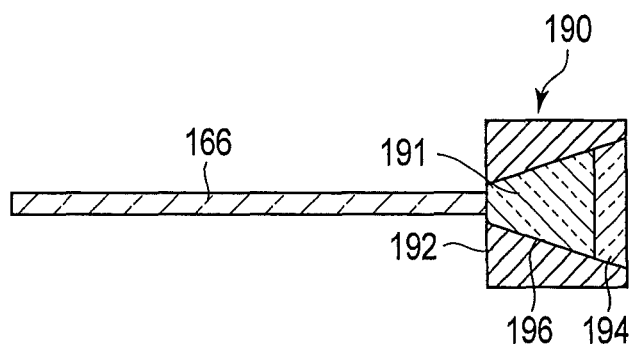
FIG. 5 is a diagram showing an overview of a configuration example of a light emitting section of the light source imaging apparatus according to the first embodiment.

A configuration example of the light emitting portion 190 according to the present embodiment is shown in FIG. 5. FIG. 5 is a schematic diagram showing the light emitting portion 190 and the distal end of the exit side optical fiber 166 in a plane passing through the central axis of the exit side optical fiber 166. The light emitting portion 190 has a holder 192 having a truncated-cone-shaped through-hole provided at the end of the exit side optical fiber 166. A diffusion plate 194 in the shape of a lid is attached to an opening on the side of the through-hole of the holder 192 opposite to the side to which the exit side optical fiber 166 is connected. For the diffusion plate 194, it is possible to use, for example, a transparent resin in which alumina particles higher in refractive index than the resin are dispersed, a transparent resin in which structures such as minute air bubbles lower in refractive index than the resin are dispersed, frosted glass having minute depressions and projections on the surface, and a compound of the above. It is also possible to apply various other known members as the diffusion plate 194. If the diffusion plate 194 is located in the vicinity of the end of the exit side optical fiber 166, the diffusion plate 194 may be, for example, deformed by the heat of the laser light. Thus, the diffusion plate 194 is located at an appropriate distance from the end of the exit side optical fiber 166.

A reflecting mirror 196 is provided on the inner surface of the through-hole. A cavity 191 inside the through-hole surrounded by the end of the exit side optical fiber 166, the diffusion plate 194, and the reflecting mirror 196 is filled with a resin transparent to the laser light emitted from the first to fourth semiconductor laser light sources. Glass may be used instead of the resin to fill the cavity 191. The exit side optical fiber 166 and the holder 192 are assembled to maintain an optical positional relation by unshown members such as a ferrule and a sleeve.

The laser light guided by the exit side optical fiber 166 and emitted from the exit end of the exit side optical fiber 166 comes into the transparent resin in the cavity 191, travels with a divergence angle corresponding to, for example, the NA of the exit side optical fiber 166, the refractive index of the resin in the cavity 191, and the wavelength of the laser light, and enters the diffusion plate 194. A portion of the laser light that has entered the diffusion plate 194 is emitted to the outside through the diffusion plate 194, and the other portion of the light is reflected backward and scattered and then travels. The laser light that has been reflected and scattered backward is reflected by the truncated-cone-shaped reflecting mirror 196, and again travels forward. Some of this light is emitted to the outside, and the remainder of the light is again emitted backward. While a series of these phenomena is repeated, the laser light as a primary light that has entered the light emitting portion 190 becomes a secondary light in which the radiation angle, light distribution, and coherency that are the optical characteristics of the laser light are adjusted by the light emitting portion 190. The size of the light radiating point is the size of the outer surface of the diffusion plate 194. That is, the size of the light radiating point is the size of the core portion of the exit side optical fiber 166 when the light emitting portion 190 is absent, but the size of the light radiating point is increased by the light emitting portion 190 in the present embodiment.

According to the present embodiment, the light emitting portion 190 allows the distributions of the laser light emitted from the first to fourth semiconductor laser light sources to be substantially uniform, so that a safe, low-coherency, and satisfactory illumination light without color unevenness can be obtained.

Figure 6:
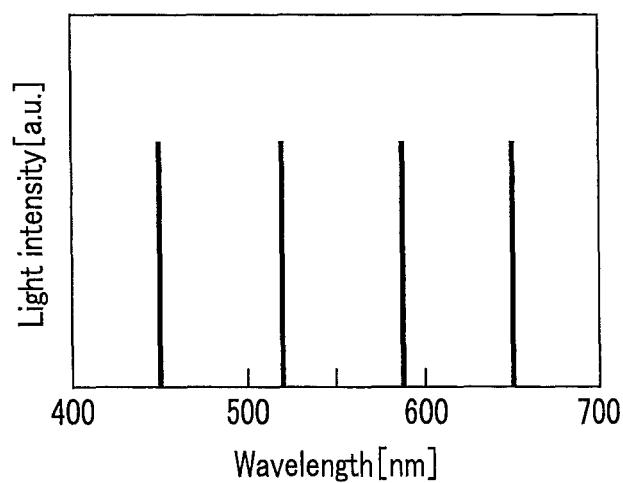
FIG. 6 is a diagram showing an example of wavelength characteristics of emitted light of the light source imaging apparatus according to the first embodiment.

A schematic diagram of the spectrum of the illumination light as a secondary light emitted from the light emitting portion 190 according to the present embodiment is shown in FIG. 6. As shown in this drawing, the wavelengths and intensity ratio of the laser light do not considerably change compared to the wavelengths and intensity ratio of the laser light emitted from the first to fourth semiconductor laser light sources, and four kinds of narrow-band light are emitted as illumination light.

The configuration of the light emitting portion 190 shown here is one example, and various modifications can be made. For example, it is possible to make various modifications; the entire light emitting portion may slightly vibrate to sufficiently reduce coherency and thereby inhibit the occurrence of speckles, or another optical system for speckle measures according to a conventional art may be provided at the subsequent stage of the light emitting portion. It is also possible to provide two or more diffusion plates or provide another diffusion plate at the subsequent stage of the light emitting portion. It is also possible to use an optical system such as a lens for fine adjustment of the light distribution and the radiation angle.

The imaging unit 184 is described in detail. The light source imaging apparatus 100 is expected to be inserted in the internal space of the observation target 900, and used in an environment where the intensity of external light such as natural light or room light is negligible compared with the intensity of the illumination light. Therefore, the imaging unit 184 acquires an image of the observation target 900 illuminated by the reflected light and scattered light of the illumination light emitted from the light emitting portion 190 toward the observation target 900.

The imaging unit 184 can acquire images separately and independently for the respective three wavelength regions: the red region (R region), the green region (G region), and the blue region (B region). That is, the imaging unit 184 has three kinds of light detection elements: R light detection elements for detecting the R region, G light detection elements for detecting the G region, and B light detection elements for detecting the B region. As in a widely used general image sensor, a large number of the respective R light detection elements, G light detection elements, and B light detection elements are arranged in matrix form in the image sensor provided in the imaging unit 184. This arrangement conforms to, for example, a Bayer array.

Figure 7:
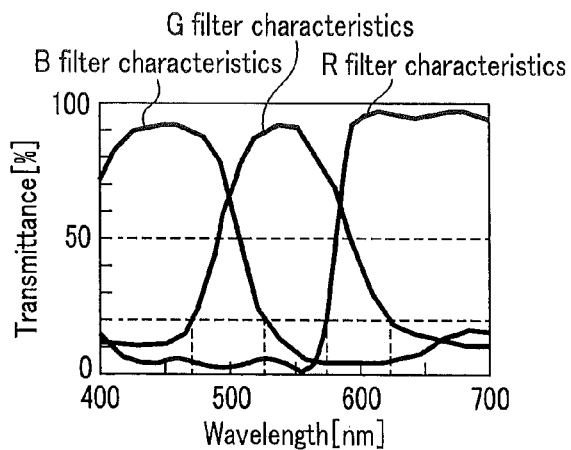
FIG. 7 is a graph showing an example of wavelength characteristics of a filter provided in an imaging unit of the light source imaging apparatus according to the first embodiment.

Each of the light detection elements includes a filter which transmits the light in each region, and a light detection element. The spectral characteristics of the R filter provided in the R light detection element, the spectral characteristics of the G filter provided in the G light detection element, and the spectral characteristics of the B filter provided in the B light detection element are shown in FIG. 7. As shown in FIG. 7, the filters provided in the imaging unit 184 according to the present embodiment are primary-color filters for general image sensors. The light transmittance of each of the R, G, and B filters has a peak at a predetermined wavelength, and the transmittance gradually decreases substantially from this peak. All the filters have almost no regions where the transmittance is zero, and all the filters have several percent to about ten percent of transmittance in a wide region of visible light. It can be said that several percent to about ten percent of transmittance is at a negligible level in the acquisition of a color image. The wavelength characteristics shown in FIG. 7 are general but are examples. Even if a filter having other characteristics is used in the imaging unit 184, components other than the imaging unit 184 such as the light source section 120 can be properly modified accordingly as in the following explanation.

Figure 8:
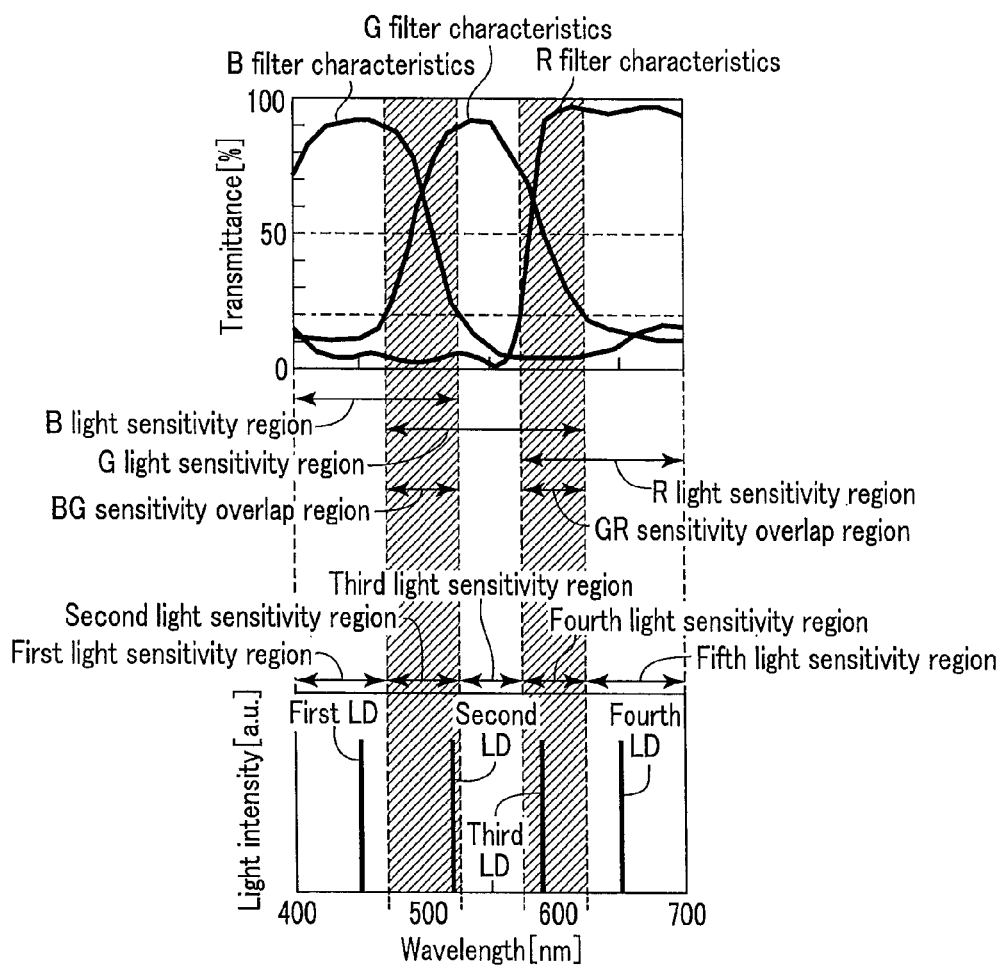
FIG. 8 is a graph showing an example of wavelength characteristics associated with the light source imaging apparatus according to the first embodiment.
Figure 9A:
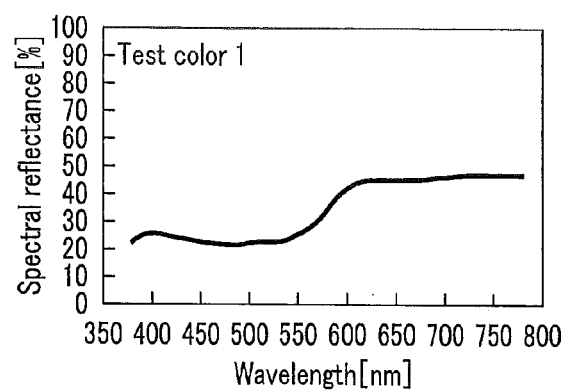
FIG. 9A is a graph showing a spectrum of a spectral reflectance of a test color 1 used in a color rendering properties evaluation.
Figure 9B:
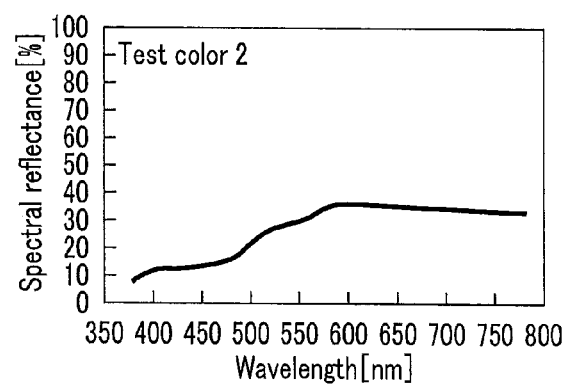
FIG. 9B is a graph showing a spectrum of a spectral reflectance of a test color 2 used in the color rendering properties evaluation.
Figure 9C:
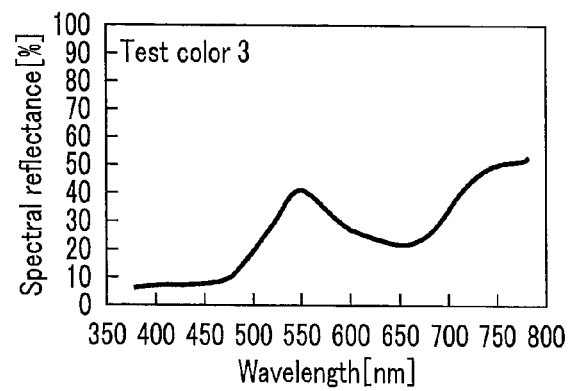
FIG. 9C is a graph showing a spectrum of a spectral reflectance of a test color 3 used in the color rendering properties evaluation.
Figure 9D:
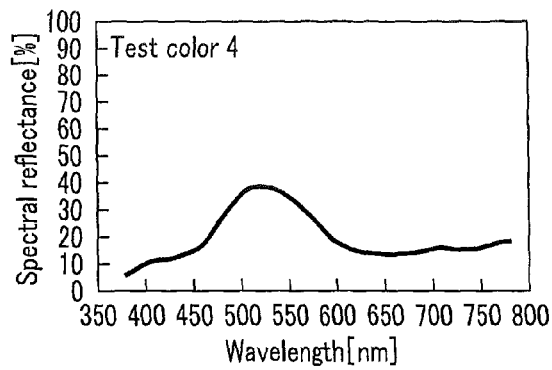
FIG. 9D is a graph showing a spectrum of a spectral reflectance of a test color 4 used in the color rendering properties evaluation.
Figure 9E:
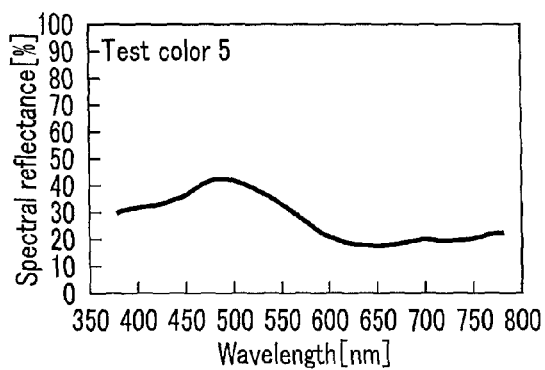
FIG. 9E is a graph showing a spectrum of a spectral reflectance of a test color 5 used in the color rendering properties evaluation.
Figure 9F:
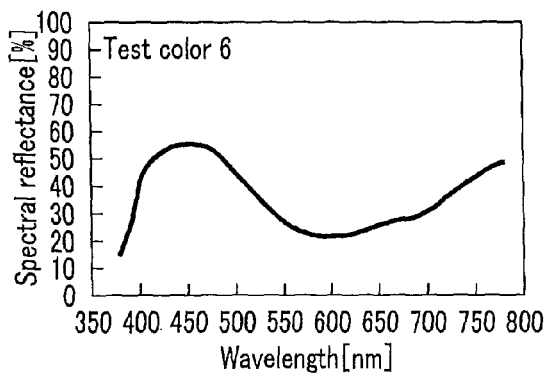
FIG. 9F is a graph showing a spectrum of a spectral reflectance of a test color 6 used in the color rendering properties evaluation.
Figure 9G:
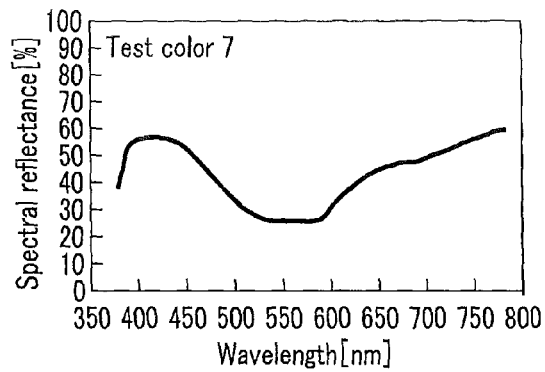
FIG. 9G is a graph showing a spectrum of a spectral reflectance of a test color 7 used in the color rendering properties evaluation.
Figure 9H:
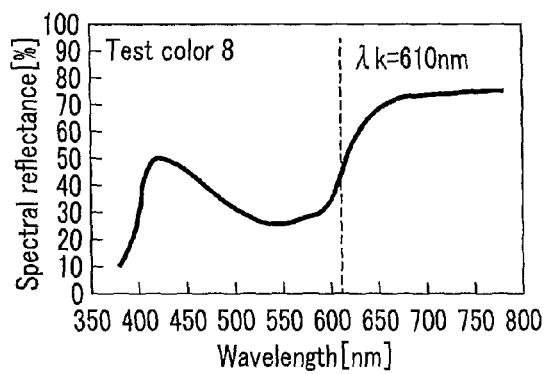
FIG. 9H is a graph showing a spectrum of a spectral reflectance of a test color 8 used in the color rendering properties evaluation.
Figure 9I:
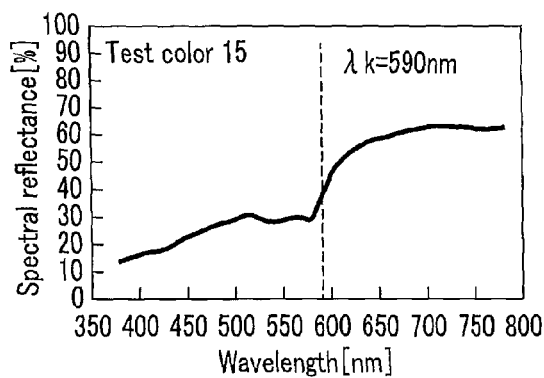
FIG. 9I is a graph showing a spectrum of a spectral reflectance of a test color 15 used in the color rendering properties evaluation.

In the present embodiment, a wavelength region having a transmittance of 20 percent or more is defined as the sensitivity region of each light detection element. That is, as shown in FIG. 8, a B light sensitivity region which is the light sensitivity region of the B light detection element is at 400 to 525 nm, a G light sensitivity region which is the light sensitivity region of the G light detection element is at 470 to 625 nm, and an R light sensitivity region which is the wavelength sensitivity region of the R light detection element is at 570 to 700 nm. The B light sensitivity region and the G light sensitivity region overlap at 470 to 525 nm, and this region is referred to as a BG sensitivity overlap region. Similarly, the G light sensitivity region and the R light sensitivity region overlap at 570 to 625 nm, and this region is referred to as a GR sensitivity overlap region. The light having a wavelength included in the BG sensitivity overlap region is detected to a non-negligible degree in both the B light detection element and the G light detection element.

Similarly, the light having a wavelength included in the GR sensitivity overlap region is detected to a non-negligible degree in both the G light detection element and the R light detection element.

The transmittance of each filter according to the present embodiment at each wavelength, and the wavelength characteristics of the four semiconductor laser light sources are shown in FIG. 8. As shown in FIG. 8, in the present embodiment, the blue-green laser light having a wavelength of 520 nm emitted from the second semiconductor laser light source (LD) 122 is included in the BG sensitivity overlap region, and its reflected light and other light are detected by both the B light detection element and the G light detection element. The orange laser light having a wavelength of 590 nm emitted from the third semiconductor laser light source (LD) 123 is included in the GR sensitivity overlap region, and its reflected light and other light are detected by both the G light detection element and the R light detection element. In other words, the B light detection element is a multiple light detection element for detecting the blue laser light having a wavelength of 450 nm output from the first semiconductor laser light source (LD) 121 and the blue-green laser light having a wavelength of 520 nm output from the second semiconductor laser light source (LD) 122. The G light detection element is a multiple light detection element for detecting the blue-green laser light having a wavelength of 520 nm output from the second semiconductor laser light source (LD) 122 and the orange laser light having a wavelength of 590 nm output from the third semiconductor laser light source (LD) 123. The R light detection element is a multiple light detection element for detecting the orange laser light having a wavelength of 590 nm output from the third semiconductor laser light source (LD) 123 and the red laser light having a wavelength of 650 nm output from the fourth semiconductor laser light source (LD) 124.

The four kinds of laser light used in the light sources described in Jpn. Pat. Appln. KOKAI Publication No. 10-286235 are a blue laser light of 441.6 nm, a green laser light of 537.8 nm, and two kinds of red laser light of 636.0 nm and 632.8 nm. In this case, the blue laser light of 441.6 nm is detected solely by the B light detection element, the green laser light of 537.8 nm is detected solely by the G light detection element, and the two kinds of red laser light of 636.0 nm and 632.8 nm are detected solely by the R light detection element.

The imaging unit 184 is supplied with electric power through an unshown electric wiring line, and is instructed to start/end imaging. The imaging unit 184 starts imaging in accordance with the instruction to start imaging, and receives light of the illumination light reflected and scattered by the observation target. Each light detection element of the imaging unit 184 transmits a signal corresponding to the wavelength characteristics of the filter provided in each element as image information to the image processing circuit 144 through the image signal line 186.

The image processing circuit 144 subjects the received image information to proper image processing. The image processing circuit 144 outputs the processed information to the control unit 141 to display an image on the display unit 147 and to record the image information in the recording unit 148.

Now, the operation of the light source imaging apparatus 100 according to the present embodiment is described. For example, the control unit 141 causes the light source control circuit 142 to control the operations of the first semiconductor laser light source 121, the second semiconductor laser light source 122, the third semiconductor laser light source 123, and the fourth semiconductor laser light source 124 in accordance with an instruction by the user input from the input unit 146 and information regarding the image processed by the image processing circuit 144. That is, the light source control circuit 142 outputs a control signal calculated by the use of the information input from the control unit 141 to the first drive circuit 131, the second drive circuit 132, the third drive circuit 133, and the fourth drive circuit 134 via the control signal lines 139.

The first to fourth drive circuits supply electric power to the first to fourth semiconductor laser light sources to operate the first to fourth semiconductor laser light sources with the timings and light intensity calculated by the light source control circuit 142 in accordance with the control signals input from the light source control circuit 142, respectively. The first to fourth semiconductor laser light sources emit laser light having specific wavelengths by the electric power input from the first to fourth drive circuits, respectively.

The four kinds of laser light different in wavelength from one another emitted from the first to fourth semiconductor laser light sources enter the optical combiner section 150 via the entrance side optical fiber 162, respectively. The four kinds of laser light different in wavelength that have entered the optical combiner section 150 are optically coupled in the optical combiner section 150, and enter one exit side optical fiber 166. The four kinds of laser light that have entered the exit side optical fiber 166 are guided by the exit side optical fiber 166, and enter the light emitting portion 190 provided at the distal end of the insertion portion 180. The light emitting portion 190 converts the laser light guided by the exit side optical fiber 166 into an illumination light which is a diffused light as described above. The light emitting portion 190 emits the illumination light toward the observation target 900.

The characteristics of the illumination light emitted from the light emitting portion 190 can be adjusted by the respective emission intensity and timings of the first to fourth semiconductor laser light sources determined by the light source control circuit 142. For example, the light emitting portion 190 can also emit light in the order of red, orange, blue-green, and blue. The light emitting portion 190 can also emit a particular combination of light at a particular timing.

The illumination light emitted from the light emitting portion 190 has the following characteristics. The illumination light is a narrow-band light, and the wavelength of the illumination light corresponds to blue, blue-green, orange, and red. The distribution of the illumination light is fully diffused, and the illumination light is a diffused light sufficiently low in coherency. Further, in the explanation below, the laser light of the respective colors are simultaneously emitted, and are equal to each other in intensity. Such an illumination light, when applied to the observation target 900, becomes a reflected and scattered light corresponding to the spectral reflectance of the observation target. A component of this reflected and scattered light that travels to the imaging unit 184 provided at the distal end of the insertion portion 180 enters this imaging unit 184. The reflected and scattered light that has entered the imaging unit 184 is detected as image information by the imaging unit 184.

As shown in FIG. 8, the B light detection element of the imaging unit 184 detects the light based on the blue laser light having a wavelength of 450 nm output from the first semiconductor laser light source (LD) 121 and the light based on the blue-green laser light having a wavelength of 520 nm output from the second semiconductor laser light source (LD) 122. The G light detection element of the imaging unit 184 detects the light based on the blue-green laser light having a wavelength of 520 nm output from the second semiconductor laser light source (LD) 122 and the light based on the orange laser light having a wavelength of 590 nm output from the third semiconductor laser light source (LD) 123. The R light detection element of the imaging unit 184 detects the light based on the orange laser light having a wavelength of 590 nm output from the third semiconductor laser light source (LD) 123 and the light based on the red laser light having a wavelength of 650 nm output from the fourth semiconductor laser light source (LD) 124.

In the present embodiment, the narrow-band light of four colors included in the illumination light emitted from the light emitting portion 190 are substantially equal in intensity. That is, when the spectral reflectance of the observation target 900 is constant, the light intensity detected in the light detection elements of the imaging unit 184 are designed to be substantially equal. Therefore, when the spectral reflectance is not constant, the light intensity detected in the light detection elements of the imaging unit 184 show an intensity ratio corresponding to spectral reflectances at the wavelengths of the narrow-band light with λnb1 to λnb4 detected by the light detection elements.

The reflected and scattered light of the illumination light that has entered the imaging unit 184 is converted into an electric signal by the image sensor and an electric circuit included in the imaging unit 184. An image signal generated in the imaging unit 184 is transmitted to the image processing circuit 144 via the image signal line 186. The image processing circuit 144 subjects the image signal input from the imaging unit 184 to image processing by using information regarding the light control in the light source control circuit 142 and information regarding the wavelengths and intensities of the narrow-band light, and outputs the image signal to the control unit 141. The image signal processed in the image processing circuit 144 is, for example, displayed on the display unit 147 and recorded in the recording unit 148.

Here, how to select the wavelengths of the laser light as the narrow-band light of the light source imaging apparatus 100 according to the present embodiment is described. A general color rendering index Ra is generally used as an index to convert color reproducibility into a numerical value. The general color rendering index is defined by Japanese Industrial Standard, JIS Z 8726 "Method of Specifying Colour Rendering Properties of Light Sources" or by International Commission on Illumination CIE No. 13-2 (1974) "Method of Measuring and Specifying Colour Rendering Properties of Light Sources," the entire contents of all of which are incorporated herein by reference. Test colors (color samples) of 15 kinds different in spectral reflectance are used to evaluate a color rendering index. Color rendering indexes R1 to R15 are measured for these test colors. The test colors 1 to 8 corresponding to the color rendering indexes R1 to R8 are colors based on objects in nature, and the test colors 9 to 14 corresponding to the color rendering indexes R9 to R14 are colors that are relatively high in chroma. The test color 15 corresponding to the color rendering index R15 is a color based on the skin of a Japanese person. The general color rendering index that is most widely used as the index of color reproducibility is the average of the color rendering indexes R1 to R8.

FIG. 9A to FIG. 9I show spectra of spectral reflectances of the test colors 1 to 8 and 15, respectively. In FIG. 9A to FIG. 9I, the horizontal axes show wavelengths from 350 nm in an ultraviolet region to 800 nm in an infrared region. The vertical axes show the spectral reflectance. Here, the spectral reflectance represents the rate of the light reflected when applied to an object as reflectivity (%) in relation to wavelength. As shown in FIG. 9A to FIG. 9I, in all the test colors, the changes of the spectral reflectances responsive to the wavelength are smooth, and no parts that change in a stepped form are found at adjacent wavelengths, in a range of 400 to 700 nm which is a general visible light region. It can be said that when a light detection unit such as the imaging unit 184 can more accurately detect the difference of the spectral reflectances resulting from the wavelengths shown in FIG. 9A to FIG. 9I, color reproducibility by this light detection unit is higher.

The spectral reflectance relatively sharply changes with the wavelength in the visible light region in the vicinity of 610 nm in the case of the test color 8 and in the vicinity of 590 nm in the case of the test color 15. The wavelength at which the spectral reflectance considerably changes is a sharp wavelength λk. For example, the sharp wavelength λk=610 nm in the test color 8 (see FIG. 9H), and the sharp wavelength λk=590 nm in the test color 15 (see FIG. 9I). If the change of the spectral reflectance in each test color is considered, the change rate of the spectral reflectance is about 1%/nm in the vicinity of 610 nm in the case of the test color 8 and in the vicinity of 590 nm in the case of the test color 15. Except in these two parts, the changes of the spectral reflectances in the test colors 1 to 8 and 15 are less than or equal to about 0.5%/nm.

Color reproducibility is considered based on this change of the spectral reflectance. It is considered that when the imaging unit 184 can detect a difference of about 20% in spectral reflectance, color reproducibility of the image to be obtained significantly improves. When the observation target is illuminated by a narrow-band light such as a laser light, the light detection unit can only detect the spectral reflectance of the wavelength of the illumination. Therefore, it is necessary to illuminate with light having wavelengths which are about 20% different in spectral reflectance to detect a difference of about 20% in spectral reflectance.

As shown in FIG. 9A to FIG. 9I, if the change of the spectral reflectance is about 0.5%/nm, the wavelength difference between the illumination light based on two kinds of narrow-band light needs to be about 40 nm or more to illuminate with light having wavelengths which are about 20% different in spectral reflectance for a significant improvement in color reproducibility. Similarly, if the change of the spectral reflectance is about 1%/nm, the wavelength difference between two kinds of narrow-band light needs to be about 20 nm or more for a significant improvement in color reproducibility. In contrast, in a light source device used in combination with an image sensor having light detection elements different in spectral characteristics as in the imaging unit 184 described above, the wavelengths of the two kinds of narrow-band light are preferably included in one light sensitivity region by one light detection element.

The index of the wavelength difference can be adjusted suitably for the purpose of the light source device and the number of kinds of laser light that are narrow-band light. However, even if the number of kinds of laser light is sufficiently large and the purpose is to accurately detect the difference of spectral reflectances, it is difficult to consider that the wavelength difference of the laser light significantly improves color reproducibility when the wavelength difference is 10 nm or less. In a light source device in which a finite number of kinds of laser light are combined, the wavelength difference is preferably about 20 nm or more for improvement in color reproducibility, and a wavelength difference of 40 nm or more is considered to significantly improve color reproducibility.

Moreover, to efficiently improve color reproducibility by the minimum number of light sources, it is preferable to set the wavelengths of the laser light that are narrow-band light across the sharp wavelength λk at which the spectral reflectance of the principle observation target considerably changes. Particularly in the above-mentioned light source device used in combination with the image sensor having the light detection elements different in spectral characteristics, it is preferable to set the wavelengths of the laser light in one light sensitivity region by one light detection element and across the sharp wavelength λk at which the spectral reflectance of the observation target considerably changes. When the wavelengths of the laser light are set across the sharp wavelength λk at which the spectral reflectance of the observation target considerably changes, color reproducibility may be significantly improved even if the wavelength difference of the laser light is small. It is generally preferable to set the wavelength difference of the laser light to 40 nm or more. However, when the wavelengths of the laser light are set across the sharp wavelength λk, color reproducibility may be significantly improved even if the wavelength difference is about 20 nm or 10 nm.

Referring to FIG. 9A to FIG. 9I, when the light source imaging apparatus 100 is set to have versatility, the wavelengths of the laser light are set in one light sensitivity region by one light detection element and across the sharp wavelength λk=600 nm, so that an improvement in the color rendering index which is the index of color reproducibility can be expected. When the purpose is limited, for example, when the color of the skin of a Japanese person is observed, the wavelengths of the laser light are set in one light sensitivity region by one light detection element and across the sharp wavelength λk=590 nm, so that an improvement in the color rendering index which is the index of color reproducibility can be expected. For other limited purposes, the wavelengths of the laser light are set by the use of the sharp wavelength λk acquired by measuring the spectral reflectance of the observation target, so that an improvement in the color rendering index which is the index of color reproducibility can be expected.

Thus, when two laser light sources are provided and color reproducibility thereby improves compared to that in the case of one laser light source, the wavelengths of these two laser light sources are referred to as "being discrete in wavelength". The wavelength difference of two laser light sources that are discrete in wavelength is referred to as an effective wavelength gap.

It is self-evident that the color reproducibility of the light source device configured to be able to emit many kinds of laser light is high. That is, if, for example, hundred or more laser light can be arranged every several nm in the visible light region, color reproducibility can be considerably higher. However, the wavelength of the light emitted by a generally distributed laser light source is limited to a particular value, and laser light sources which emit other wavelengths are unavailable or are expensive even if available. If a large number of laser light sources are used, various problems can occur, such as higher cost, higher power consumption, and size increase in the whole apparatus. Therefore, the smallest possible number of laser light sources is preferable.

In view of the circumstances, in the present embodiment, the number of laser light sources is determined to be four which is the minimum required number to obtain desired color reproducibility. Three of the four laser light sources are selected from generally distributed semiconductor laser light sources. Wavelength selection criteria for laser light sources in the present embodiment are shown below.

(1) The number of wavelengths of the laser light is four which is the minimum required number to obtain predetermined color reproducibility.

(2) As shown in FIG. 8, the R light sensitivity region, the G light sensitivity region, and the B light sensitivity region of the imaging unit 184 each include at least one wavelength, preferably two or more wavelengths of the laser light sources.

(3) The wavelength difference of the laser light sources is equal to or more than the effective wavelength gap, and is 40 nm or more at which the wavelengths are considerate to be discrete.

(4) The wavelengths of the laser light are determined so that two wavelengths of laser light are provided across the sharp wavelength λk at which the spectral reflectances of the test colors 1 to 8 and 15 sharply change.

(5) The wavelength of the commercially available laser light source is used.

In accordance with the above, the wavelengths of the first to fourth semiconductor laser light sources are selected. The wavelengths of the first to fourth semiconductor laser light sources according to the present embodiment satisfy (1) to (5) as below. That is, (1) the number of wavelengths of the laser light is four: the blue laser of the first semiconductor laser light source 121, the blue-green laser of the second semiconductor laser light source 122, the orange laser of the third semiconductor laser light source 123, and the red laser of the fourth semiconductor laser light source 124.

(2) The B light sensitivity region includes the wavelengths of the first semiconductor laser light source 121 and the second semiconductor laser light source 122. The G light sensitivity region includes the wavelengths of the second semiconductor laser light source 122 and the third semiconductor laser light source 123. The R light sensitivity region includes the third semiconductor laser light source 123 and the fourth semiconductor laser light source 124.

(3) The wavelength difference between the first semiconductor laser light source 121 and the second semiconductor laser light source 122 is 70 nm. The wavelength difference between the second semiconductor laser light source 122 and the third semiconductor laser light source 123 is 70 nm. The wavelength difference between the third semiconductor laser light source 123 and the fourth semiconductor laser light source 124 is 60 nm. All the wavelength differences are 40 nm or more. When the visible light region is 400 to 700 nm, the wavelength difference between 400 nm at one end of the visible light region and the wavelength of the first semiconductor laser light source 121 is 50 nm. The wavelength difference between 700 nm at the other end of the visible light region and the wavelength of the fourth semiconductor laser light source 124 is 50 nm. Both the wavelength differences are 40 nm or more. That is, the wavelength of the first semiconductor laser light source 121 and the wavelength of the fourth semiconductor laser light source 124 are 40 nm or more apart from 400 nm and 700 nm that are the limits of the visible light region in which a human being has visibility, so that wavelengths useful in color reproducibility are selected.

(4) The orange laser light of 590 nm (the third semiconductor laser light source 123) and the red laser light of 650 nm (the fourth semiconductor laser light source 124) are provided across the sharp wavelength λk=600 nm at which the spectral reflectances of the test colors 8 and 15 sharply change.

(5) The first to fourth semiconductor laser light sources are on the market and are all readily available.

The part of the B light sensitivity region except for the G light sensitivity region is referred to as a first light sensitivity region. The BG sensitivity overlap region is referred to as a second light sensitivity region. The part of the G light sensitivity region except for the B light sensitivity region and the R light sensitivity region is referred to as a third light sensitivity region. The GR sensitivity overlap region is referred to as a fourth light sensitivity region. The part of the R light sensitivity region except for the G light sensitivity region is referred to as a fifth light sensitivity region.

The present embodiment not only takes into consideration color reproducibility used for all purposes but also takes into consideration an application in which the observation target is a living body. Thus, the present embodiment is designed to place relatively high importance on red color reproducibility (the test colors 8 and 15). That is, the first semiconductor laser light source 121 is provided to correspond to the first light sensitivity region, the second semiconductor laser light source 122 is provided to correspond to the region in which the second light sensitivity region and the third light sensitivity region are combined, the third semiconductor laser light source 123 is provided to correspond to the fourth light sensitivity region, and the fourth semiconductor laser light source 124 is provided to correspond to the fifth light sensitivity region. The laser light sources are provided as described above, so that it is possible to provide a light source device which improves all-purpose color reproducibility and which is suitably applied to a living body. While one laser light source is provided for each of the first, fourth, and fifth light sensitivity regions, one laser light source is only provided for the second and third light sensitivity regions. This is because when a living body is the observation target, it is difficult to assume a considerable change in spectral reflectance in the blue-green to green regions, and importance is placed on minimization of the number of laser light sources while color reproducibility in the blue-green to green regions is relatively disregarded. When importance is also placed on the color reproducibility in the blue-green to green regions, one laser light source should be provided for each of the second and third light sensitivity regions.

A configuration in which one laser light is used for each of the three red, green, and blue wavelength regions is known as a light source device that uses a conventional general laser light. In the light source device according to Jpn. Pat. Appln. KOKAI Publication No. 10-286235, the laser light of 632.8 nm (red) emitted from the He—Ne laser light source as the fourth laser light is combined with the three kinds of laser light of 441.6 nm (blue), 537.8 nm (green), and 636.0 nm (red) emitted from the He—Cd laser light source which is one white laser. Here, the difference between 636.0 nm which is the wavelength of the red light of the white laser light source and 632.8 nm which is the wavelength of the red light of the added He—Ne laser light source is 3.2 nm. This value can be said to be extremely close to about 1 nm which is the wavelength spread of the general multimode laser shown in FIG. 2. In other words, the laser light of 636.0 nm and the laser light of 632.8 nm are extremely close in wavelength, and cannot be said to be discrete in wavelength. It is therefore considered that the prior-art configuration according to Jpn. Pat. Appln. KOKAI Publication No. 10-286235 has a slight advantage of improving color reproducibility by adding the He—Ne laser light having a wavelength of 632.8 nm. Thus, it is considered that the degree of improvement in color reproducibility attributed to the use of more than one laser light is low even if laser light that is only different by several nm in wavelength is used as shown in Jpn. Pat. Appln. KOKAI Publication No. 10-286235. That is, even if laser light that is not discrete in wavelength is used in a light source device, this light source device provides a slight improvement in color reproducibility attributed to more than one laser light source therein.

As described above, according to the present embodiment, in the light source imaging apparatus 100, the imaging unit 184 has three light sensitivity regions: the R light sensitivity region, the G light sensitivity region, and the B light sensitivity region, whereas four semiconductor laser light sources are provided so that the wavelengths of two semiconductor laser light sources are included in each of the R light sensitivity region, the G light sensitivity region, and the B light sensitivity region. The wavelength difference of the laser light is 40 nm or more. In the R light sensitivity region, two kinds of laser light are provided across the wavelength λk at which the spectral reflectances sharply change in the test colors 8 and 15. Consequently, according to the light source imaging apparatus 100 in the present embodiment, sufficient color reproducibility is obtained by a small number of laser light sources even if the laser light that is discrete narrow-band light is used.

Thus, for example, the imaging unit 184 functions as an imaging unit in which wavelength sensitivity regions that are detectable wavelength bands include N (N is a natural number) kinds of light detection elements. For example, the light source section 120 functions as a light source section to emit M (M is a natural number greater than N) kinds of narrow-band light having different peak wavelengths in which the difference between the peak wavelengths is equal to or more than the effective wavelength gap. For example, the insertion portion 180 functions as an insertion portion configured to be inserted into an internal space of an object where a target exists. For example, the light emitting portion 190 functions as an illumination light emitting portion which is provided in the insertion portion and which emits an illumination light based on the guided light. For example, the entrance side optical fiber 162, the exit side optical fiber 166, and the optical combiner section 150 function as a light guide member which guides the narrow-band light emitted from the light source section to the illumination light emitting portion.

Modification of First Embodiment

A modification of the first embodiment is described. Here, the differences between the modification and the first embodiment are described, and the same parts are provided with the same reference signs and are not described. In the first embodiment, all three light detection elements included in the imaging unit 184: the R light detection element, the G light detection element, and the B light detection element are configured to be able to detect two kinds of laser light to improve the color reproducibility in the whole visible light region. That is, the wavelengths of the light emitted from the two laser light sources are included in each of the R light sensitivity region, the G light sensitivity region, and the B light sensitivity region.

In contrast, the present modification is provided with a combination of laser light sources applied when the spectrum of a spectral reflectance of the observation target is high from the green region to the red region and is low from the blue region to the blue-green region. Such an observation target is expected to be, for example, the skin of a person or the lining of a stomach. As described above, FIG. 9I shows the standard spectral reflectance of the skin of a Japanese person. In the lining of the stomach, the reflectivity of red is higher than that shown in FIG. 9I, and the spectral reflectance is lower from the blue region to the blue-green region. For such an observation target, in contrast with the first embodiment, the number of laser light sources included in the B light sensitivity region may be one, so that the laser light included in the longer wavelength side than the G light sensitivity region is preferably disposed instead.

Figure 10:
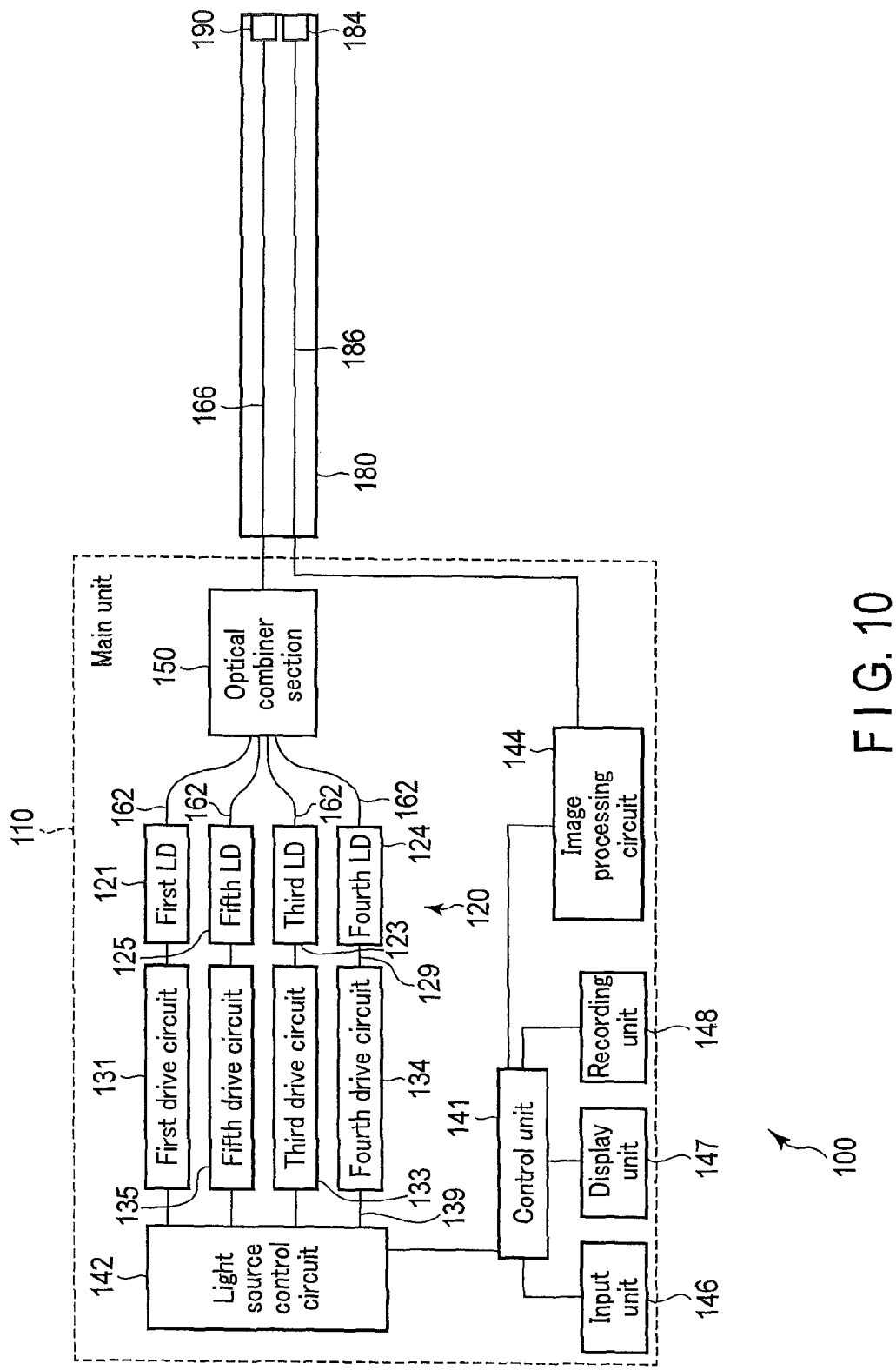
FIG. 10 is a block diagram showing an overview of a configuration example of a light source imaging apparatus according to a modification of the first embodiment.

Thus, in the present modification, as shown in FIG. 10, the light source section 120 of the light source imaging apparatus 100 is provided with a fifth semiconductor laser light source 125 which emits a green light having a wavelength of 532 nm, instead of the second semiconductor laser light source 122 which emits a blue-green light having a wavelength of 520 nm. The light source imaging apparatus 100 is provided with, instead of the second drive circuit 132, a fifth drive circuit 135 which is connected to the fifth semiconductor laser light source 125 and which supplies a proper electric current amount to the fifth semiconductor laser light source 125. The configuration of the light source imaging apparatus 100 is similar in other respects to that in the first embodiment.

Figure 11:
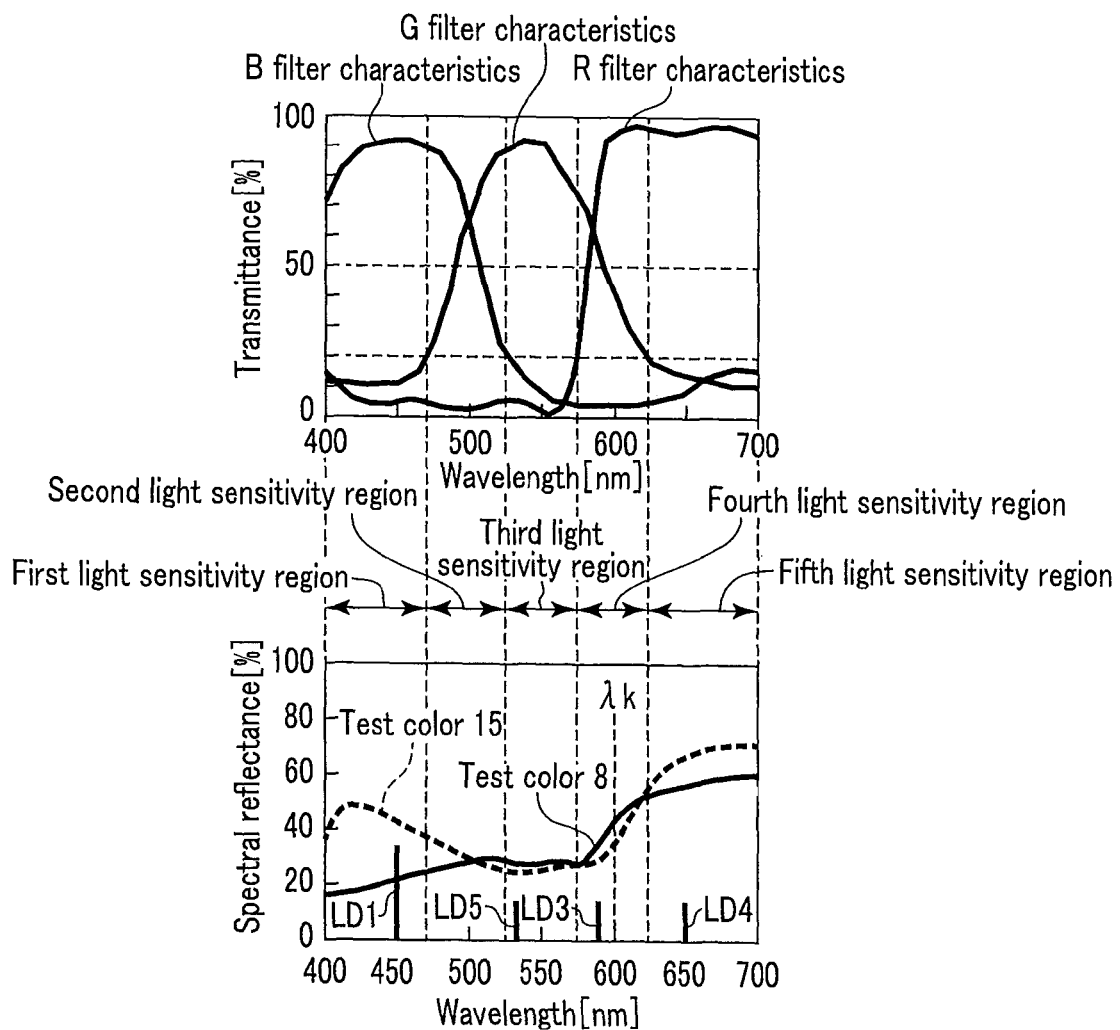
FIG. 11 is a graph showing an example of wavelength characteristics associated with the light source imaging apparatus according to the modification of the first embodiment.

As shown in FIG. 11, in the present modification, the laser light included in the B light sensitivity region is only the blue laser of 450 nm emitted from the first semiconductor laser light source 121. The laser light included in the G light sensitivity region constitute two colors: a green laser light of 532 nm emitted from the fifth semiconductor laser light source 125, and an orange laser light of 590 nm emitted from the third semiconductor laser light source 123. The laser light included in the R light sensitivity region constitute two colors: an orange laser light of 590 nm emitted from the third semiconductor laser light source 123, and a red laser light of 650 nm emitted from the fourth semiconductor laser light source 124. That is, in the present modification, the G light detection element and the R light detection element are multiple light detection elements for detecting two kinds of narrow-band light, whereas the B light detection element is a light detection element for detecting a single narrow-band light. Thus, if all the intensity of the laser light respectively emitted from the first semiconductor laser light source 121, the fifth semiconductor laser light source 125, the third semiconductor laser light source 123, and the fourth semiconductor laser light source 124 are substantially equal as has been described with reference to FIG. 6, the following problem occurs: Even if the spectral reflectance of the observation target is constant without changing with the wavelength, the light intensity detected by the B light detection element is about half of the light intensity detected by the G light detection element and the R light detection element. Thus, in the present modification, the light intensity ratio between the first semiconductor laser light source 121, the fifth semiconductor laser light source 125, the third semiconductor laser light source 123, and the fourth semiconductor laser light source 124 is set to 2:1:1:1.

The present modification can be used for a vital observation for the skin of a person or the lining of a stomach as described above. Thus, in the first embodiment, one laser light is included in the above-mentioned second light sensitivity region, and no laser light is included in the third light sensitivity region. However, in the present modification, one laser light is included in the third light sensitivity region, and no laser light is included in the second light sensitivity region.

According to the present modification, in contrast with the first embodiment, the light detected by the G light detection element is on the longer wavelength side (red side), resulting that the color reproducibility is higher from the green region to the red region than in the first embodiment. Regarding the fifth semiconductor laser light source 125 which emits the green laser light of 532 nm, the laser light of 532 nm is close to pure green, so that high-output products such as a projector are on the market for various purposes. Thus, the fifth semiconductor laser light source 125 is available at a low price. That is, a higher intensity light source device can be obtained at a low price. A general light source which emits such light of 532 nm is a compound semiconductor laser light source in which an infrared semiconductor laser light source is combined with an SHG element.

Second Embodiment

A second embodiment is described. Here, the differences between the first embodiment and the second embodiment are described, and the same parts are provided with the same reference signs and are not described. In the first embodiment, the selection of the wavelengths of the laser light are determined by the spectral reflectances of the test colors 1 to 8 and 15 shown in FIG. 9A to FIG. 9I. Here, the test colors 1 to 8 are colors based on colors in nature, and the test color 15 is a color based on the color of the skin of a Japanese person. In the meantime, there are needs for observing colors higher in chroma and colorful objects. Thus, the present embodiment shows the light source imaging apparatus 100 which efficiently improves color reproducibility with a small number of laser light sources regarding colors that more sharply change in spectral reflectance than the test colors 1 to 8 and 15. The light source imaging apparatus 100 shown here observes, as a target, an object having a spectral reflectance that shows a slightly sharp spectral change in a region of 570 nm to 700 nm which is the R light sensitivity region.

Figure 12:
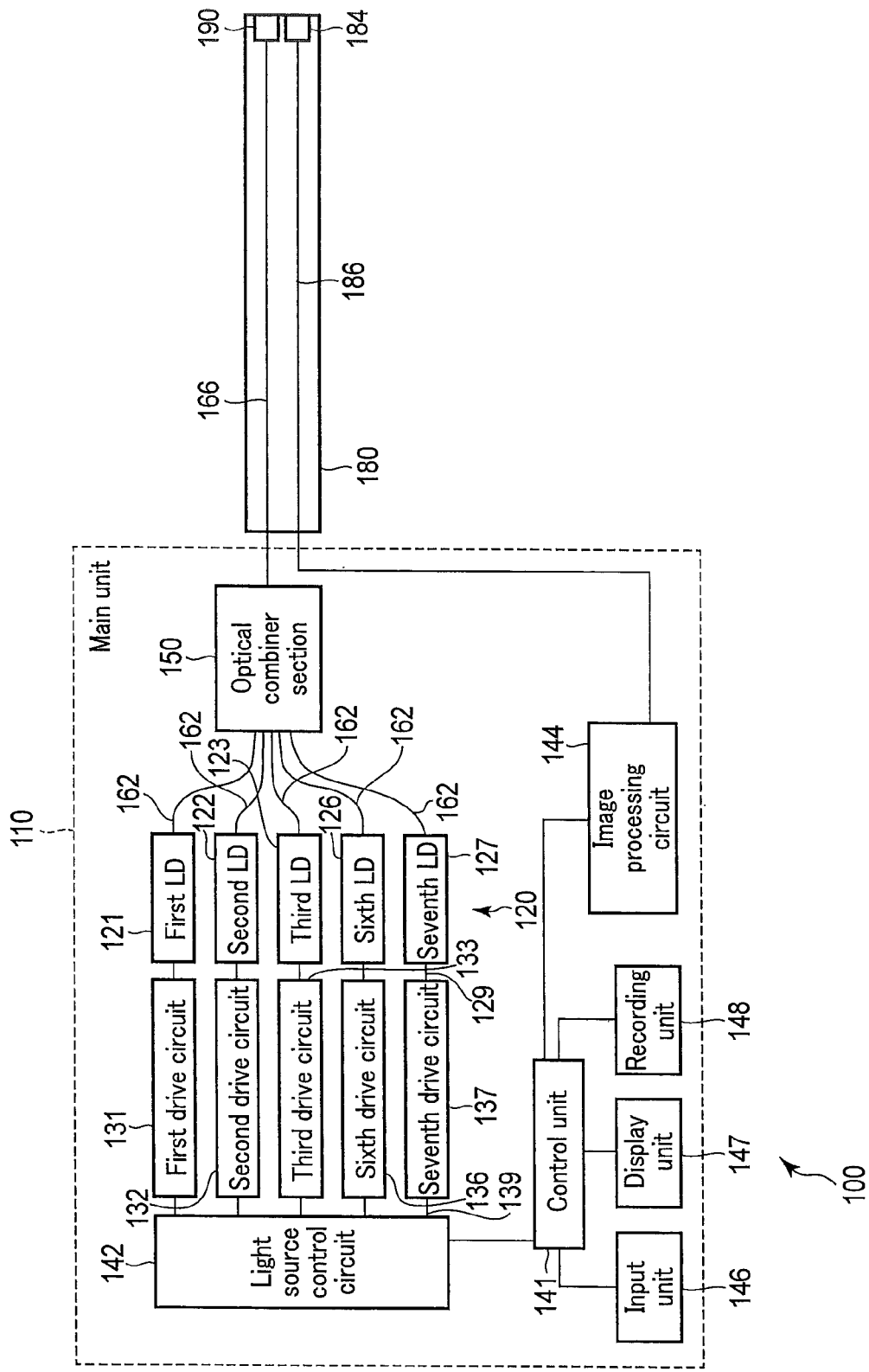
FIG. 12 is a block diagram showing an overview of a configuration example of a light source imaging apparatus according to a second embodiment.

A configuration example of the light source imaging apparatus 100 according to the present embodiment is shown in FIG. 12. In the present embodiment, the light source section 120 includes five direct-light-emitting type or compound semiconductor laser light sources: the first semiconductor laser light source 121, the second semiconductor laser light source 122, the third semiconductor laser light source 123, a sixth semiconductor laser light source 126, and a seventh semiconductor laser light source 127. Here, three semiconductor laser light sources: the third semiconductor laser light source 123, the sixth semiconductor laser light source 126, and the seventh semiconductor laser light source 127 emit laser light having wavelengths included in the R light sensitivity region (570 nm to 700 nm).

As described above, increasing the number of laser light sources tends to increase the size of the light source imaging apparatus 100 and increase costs. Thus, it is desirable that the smallest possible number of laser light sources having proper wavelengths be provided to simultaneously achieve a smaller space, lower costs, and high color reproducibility.

Thus, in the present embodiment, three wavelengths are efficiently arranged for the width W (=700−570=130 nm) of the R light sensitivity region as below.

In general, when a given natural number is q, a region having a certain length W is divided into regions having equal lengths by q points so that the length of one divisional region is W/(q+1). Therefore, q kinds of narrow-band light can also be equally arranged in the region having the length W by W/(q+1). In the present embodiment, three kinds of narrow-band light are arranged in the R light sensitivity region having a width of 130 nm, so that the width of a divisional region is 130/4=32.5 nm. Therefore, the wavelengths of the three kinds of narrow-band light are calculated at 602.5 nm, 635 nm, and 667.5 nm so that three kinds of narrow-band light are most equally arranged in the R light sensitivity region. As a result, high color reproducibility can be stably expected for observation targets having various spectral reflectances. However, it is not possible in a commercial sense to freely select any wavelength for the wavelength of a narrow-band light. That is, particular laser light sources having some wavelengths are readily available and advantageous in terms of cost. Moreover, a wavelength needs to be set in consideration of, for example, manufacturing tolerance. Thus, in the present embodiment, the wavelength gap between the narrow-band light is 16.3 nm or more which is half of 32.5 nm, and the wavelengths of the narrow-band light are selected in consideration of all of color reproducibility, the availability of the laser light sources, and costs.

The restrictions of the above-mentioned wavelengths are considered. A gap $\Delta\lambda 2$ between the peak wavelengths $\lambda nb$ of the narrow-band light adjacent in wavelength to each other is represented by Equation (1):

$$W/(2(q+1)) \leq \Delta\lambda 2 \qquad (1)$$

wherein W is the effective width of the light sensitivity region of each of the R, G, and B light detection elements, that is, the width of a region having a transmittance of 20% or more in each of the R, G, and B filter characteristics combined with the image sensor, and q (q is any natural number) is the number of kinds of narrow-band light having the peak wavelengths $\lambda nb$ included in the above light sensitivity region.

In the present embodiment, W=130 nm and q=3, so that $\Delta\lambda 2$ is 16.3 nm or more in accordance with Equation (1). Accordingly, in the present embodiment, the third semiconductor laser light source 123, the sixth semiconductor laser light source 126, and the seventh semiconductor laser light source 127 included in the R light sensitivity region are determined as below. That is, the third semiconductor laser light source 123 is a multimode SHG semiconductor laser light source which emits an orange laser light having a wavelength of 590 nm. The sixth semiconductor laser light source 126 is a multimode semiconductor laser light source which emits a vermeil laser light having a wavelength of 635 nm. The seventh semiconductor laser light source 127 is a multimode semiconductor laser light source which emits a red laser light having a wavelength of 660 nm.

Regarding the wavelength gaps between the laser light, the difference between the wavelength of the light emitted by the third semiconductor laser light source 123 and the wavelength of the light emitted by the sixth semiconductor laser light source 126 is 45 nm, and the difference between the wavelength of the light emitted by the sixth semiconductor laser light source 126 and the wavelength of the light emitted by the seventh semiconductor laser light source 127 is 25 nm. Both the differences are higher than $\Delta\lambda 2$=16.3 nm.

That is, the orange laser light having a wavelength of 590 nm emitted from the third semiconductor laser light source 123, the vermeil laser light having a wavelength of 635 nm emitted from the sixth semiconductor laser light source 126, and the red laser light having a wavelength of 660 nm emitted from the seventh semiconductor laser light source 127 are in an element narrow-band light group included in the light sensitivity region of the same R light detection element. The wavelength gap between the different kinds of laser light is $\Delta\lambda 2$, which meets the condition of Equation (1).

The light sources which emit the narrow-band light having the wavelengths included in the B light sensitivity region and the G light sensitivity region according to the present embodiment may be the first semiconductor laser light source 121 and the second semiconductor laser light source 122 shown in the first embodiment, or may be the first semiconductor laser light source 121 and the fifth semiconductor laser light source 125 shown in the modification of the first embodiment. In the present embodiment, the first semiconductor laser light source 121 and the second semiconductor laser light source 122 are used. Satisfactory color reproducibility is also obtained in the B light sensitivity region and the G light sensitivity region by the use of the first semiconductor laser light source 121 and the second semiconductor laser light source 122. Since the relatively inexpensive and high-output green laser of 532 nm is used in accordance with the G light sensitivity region by the use of the first semiconductor laser light source 121 and the fifth semiconductor laser light source 125, a bright and low-cost light source device is obtained.

While four semiconductor laser light sources are used in the first embodiment, five semiconductor laser light sources are used in the present embodiment. Accordingly, in comparison with the first embodiment, the configuration of each component is suitably changed in the present embodiment. That is, there are provided, as drive circuits, the first drive circuit 131 for driving the first semiconductor laser light source 121, the second drive circuit 132 for driving the second semiconductor laser light source 122, the third drive circuit 133 for driving the third semiconductor laser light source 123, a sixth drive circuit 136 for driving the sixth semiconductor laser light source 126, and a seventh drive circuit 137 for driving the seventh semiconductor laser light source 127. The optical combiner section 150 is a 5-in-1-out optical combiner. The configuration is similar in other respects to that in the first embodiment.

The operation of the light source imaging apparatus 100 according to the present embodiment is similar to the operation of the light source imaging apparatus 100 according to the first embodiment.

According to the present embodiment, the narrow-band light is arranged with the proper wavelength gap particularly in the light sensitivity region of the R light detection element, so that it is possible to provide a light source device which is stable and which ensures high color reproducibility in the observation of the observation target having a non-flat spectral reflectance in the above light sensitivity region. Moreover, since the number of lasers and the wavelengths are properly set, it is possible to provide a light source device in which the supply of the lasers, costs, and the size of the device are satisfactory.

Modification of Second Embodiment

A modification of the second embodiment is described. Here, the differences between the modification and the second embodiment are described, and the same parts are provided with the same reference signs and are not described. In the second embodiment, how to determine the wavelengths when the wavelengths of narrow-band light is included in the R light sensitivity region to increase color reproducibility in the light sensitivity region of one R light sensitivity region has been described. In contrast, how to determine the wavelengths to increase color reproducibility in the whole visible light region is described next.

It is generally said that the visible light region ranges from 400 nm to 700 nm. Suppose that, for example, p (p is any natural number) kinds of narrow-band light are arranged in this region. As described above, when p kinds of narrow-band light are arranged at regular intervals in a wavelength region having a certain width L, the gap therebetween is $L/(p+1)$. When the width L of the visible light region is 300 nm, each wavelength gap is found by $300/(p+1)$. In the first embodiment, p=4, so that the wavelength gap is $300 \div 5 = 60$ nm. That is, the wavelengths of the light emitted by the light sources should be 460 nm, 520 nm, 580 nm, and 640 nm so that four light sources are arranged with a uniform wavelength gap. However, as has been described in the second embodiment, the supply of the lasers, costs, and manufacturing tolerance need to be considered in the selection of the wavelengths. In other words, the wavelength gap is half or more of $L/(p+1)$ as in Equation (1) so that a light source configuration that simultaneously achieves color reproducibility, the supply of the lasers, and costs can be obtained.

That is, the width of the visible light region is L, and the minimum value of the wavelength gap between the different kinds of narrow-band light is $\Delta\lambda$. Here, all the narrow-band light included in the visible light region is collectively referred to as an all-narrow-band-light group. In this case, the narrow-band light belonging to the all-narrow-band-light group satisfy Equation (2) so that color reproducibility and the solving of problems in manufacture such as the supply of the lasers and costs can be achieved at the same time.

$$L/(2(P+1)) \leq \Delta\lambda \qquad (2)$$

When L=300 nm and p=4, in accordance with Equation (2), $\Delta\lambda$ will be 30 nm or more. In both the first embodiment and the second embodiment, the condition that $\Delta\lambda$ be 30 nm or more is satisfied. The configuration is similar in other respects to that in the first embodiment or the second embodiment.

Although the whole visible light region is observed in the case described by way of example in the above modification, the present invention is not limited to this. A region including an ultraviolet region and an infrared region may be targeted for observation depending on purposes. A region in part of the visible light region may be only targeted for observation depending on purposes. In these cases, the region width L can be modified suitably for purposes.

Third Embodiment

Figure 13:
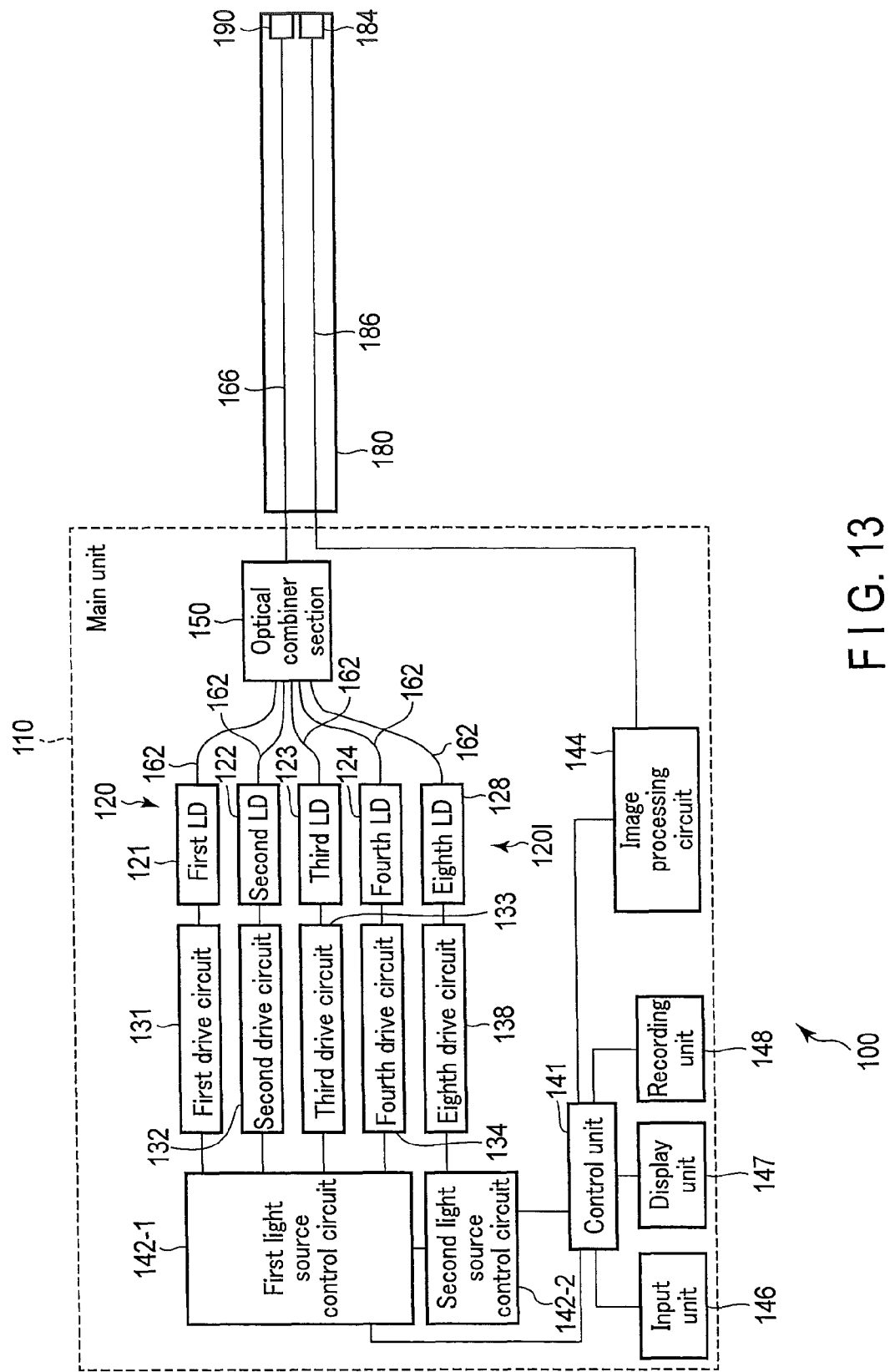
FIG. 13 is a block diagram showing an overview of a configuration example of a light source imaging apparatus according to a third embodiment.

A third embodiment is described. Here, the differences between the first embodiment and the third embodiment are described, and the same parts are provided with the same reference signs and are not described. A configuration example of the light source imaging apparatus 100 according to the present embodiment is shown in FIG. 13. As shown in this drawing, the light source imaging apparatus 100 has two light source control circuits: a first light source control circuit 142-1 and a second light source control circuit 142-2.

The first light source control circuit 142-1 is connected to the first to fourth drive circuits for driving the first to fourth semiconductor laser light sources. On the other hand, the second light source control circuit 142-2 is connected to an eighth drive circuit 138 for driving an eighth semiconductor laser light source 128. Laser light emitted from the first to fourth semiconductor laser light sources and a laser light emitted from the eighth semiconductor laser light source 128 are guided to the 5-in-1-out optical combiner section 150, guided to one exit side optical fiber 166 by this optical combiner section 150, and emitted from the light emitting portion 190. The first light source control circuit 142-1 and the second light source control circuit 142-2 are connected to each other by a communication line.

The first light source control circuit 142-1 and the part comprising the first to fourth drive circuits and the first to fourth semiconductor laser light sources are the same as those in the first embodiment. On the other hand, the second light source control circuit 142-2, the eighth drive circuit 138, and the eighth semiconductor laser light source 128 are added in comparison with the first embodiment and the second embodiment. The eighth semiconductor laser light source 128 is a light source which emits a special illumination light. The wavelength and intensity of the illumination light emitted by this eighth semiconductor laser light source 128 can be modified suitably for purposes. That is, the wavelength and others of the eighth semiconductor laser light source 128 are not limited to the wavelength and others for improving color reproducibility described in the first embodiment and the second embodiment, and are set to a wavelength necessary for a particular purpose. That is, the eighth semiconductor laser light source 128 is an exclusive light source for emitting an independent narrow-band light for the particular purpose. Thus, the light source section 120 includes the first to fourth semiconductor laser light sources, and an independent light source section 1201 includes the eighth semiconductor laser light source 128.

The eighth semiconductor laser light source 128 can be used for, for example, an observation that uses a so-called fluorescent marker which absorbs light in a particular wavelength region and then emits light having a wavelength different from this wavelength region, or a special light observation to observe, for example, the distribution of a substance which selectively absorbs light in a particular wavelength region included in an observation target. Thus, a semiconductor laser light source which emits, for example, a blue-violet laser light having a wavelength of 405 nm can be used as the eighth semiconductor laser light source 128. An imaging unit 184 may be provided for common use in both the acquisition of an image resulting from the illumination light emitted by the first to fourth semiconductor laser light sources and a special observation that uses the laser light emitted by the eighth semiconductor laser light source 128. In this case, the imaging unit 184 described in the first embodiment can be used. For the imaging unit 184, the imaging unit 184 described in the first embodiment may be used for the acquisition of an image resulting from the illumination light emitted by the first to fourth semiconductor laser light sources, whereas an additional imaging unit may be provided for the special observation that uses the laser light emitted by the eighth semiconductor laser light source 128. In the case described by way of example here, one imaging unit 184 performs the acquisition of an image resulting from the illumination light emitted by the first to fourth semiconductor laser light sources, and the special observation that uses the laser light emitted by the eighth semiconductor laser light source 128.

The operations associated with the first light source control circuit 142-1, the first to fourth drive circuits, and the first to fourth semiconductor laser light sources according to the present embodiment are similar to those in the first and second embodiments. The operations associated with the second light source control circuit 142-2, the eighth drive circuit 138, and the eighth semiconductor laser light source 128 are described.

Under the control of the second light source control circuit 142-2, the eighth drive circuit 138 supplies electric power to the eighth semiconductor laser light source 128 so that a laser light is emitted with a desired light intensity and timing. The eighth semiconductor laser light source 128 supplied with the electric power emits a blue-violet laser light having a wavelength of 405 nm. The emitted blue-violet laser light is guided to the optical combiner section 150 via the entrance side optical fiber 162. The optical combiner section 150 brings this laser light into the exit side optical fiber 166. The laser light is guided to the light emitting portion 190 by the exit side optical fiber 166, and converted into a special illumination light in the light emitting portion 190. This special illumination light is emitted toward, for example, the observation target from the light emitting portion 190.

Some of the special illumination light applied to the observation target is selectively absorbed by the observation target or wavelength-converted. Some of the reflected light and fluorescence from the observation target are received by the imaging unit 184. The imaging unit 184 transmits, to the image processing circuit 144, an image of the observation target to which the special illumination light is applied. The image processing circuit 144 subjects the transmitted image information to proper image processing. The control unit 141 displays the image after the image processing on the display unit 147 and records the image in the recording unit 148.

The first light source control circuit 142-1 and the second light source control circuit 142-2 are directly or indirectly connected to each other, and can exchange their information regarding light source control. In the present embodiment, an illumination light such as a white light controlled by the first light source control circuit 142-1 and the special illumination light controlled by the second light source control circuit 142-2 can be alternately emitted. By such illumination control, an observation image illuminated by the white light and an observation image illuminated by the special illumination light can be alternately taken. If the first light source control circuit 142-1 and the second light source control circuit 142-2 operate at the same time, it is possible to acquire an image in which two kinds of observation image, the observation image illuminated by the white light and the observation image illuminated by the special illumination light, are superimposed. Alternatively, if the white light and the special illumination light are independently turned on and off according to the purpose, or the ratio of the intensity of light to be emitted is adjusted, various observations adapted to purposes can be performed.

The independent narrow-band light which is the eighth semiconductor laser light source 128 may be only used as a special light or may be used as an illumination light for the white light. Even if the wavelength of the eighth semiconductor laser light source 128 does not meet the above-mentioned various conditions, the light emitted from the eighth semiconductor laser light source 128 only has a low effect of improving color rendering properties, and does not basically have an adverse effect that, for example, deteriorates color rendering properties. That is, the wavelength of the light emitted by the eighth semiconductor laser light source 128 and the wavelengths of the light emitted by other light sources have a slight difference and are not discrete, and these two narrow-band light have a low effect of improving color rendering properties, thus even if these two kinds of narrow-band light are considered as one narrow-band light, there is no fear that this light may have an adverse effect on color reproducibility.

According to the present embodiment, the light source imaging apparatus 100 can be used not only for a normal observation but also for a special light observation by a special spectrum suited to a purpose. In this instance, it is not necessary to greatly modify the light source imaging apparatus 100. If the light source for the white light and the light source for the special light are controlled in an integrated manner, the white light and the special light can be continuously or intermittently applied at a proper timing.

Although one eighth semiconductor laser light source 128 is included in the independent light source section 1201 for the special light observation in the present embodiment, the present invention is not limited to this. Two or more light sources for the special light observation can be provided suitably for purposes. Although the first light source control circuit 142-1 and the second light source control circuit 142-2 are provided in the configuration shown in the present embodiment, one light source control circuit may be configured to be able to control the light sources for the white light and the special light. Although the light source for the white light and the light source for the special light are provided in one main unit 110 in the example shown in the present embodiment, these light sources may be respectively provided in housings which are two main units.

Wavelengths can be selected so that some kinds of the narrow-band light that constitute a normal observation light such as the white light are used as special observation light. In this case, in selecting the other wavelengths, it is preferable to select wavelengths in consideration of the various requirements described above. Regarding one or more kinds of narrow-band light to be used as the special illumination light, wavelength selection suited to their purposes has priority, so that the above-mentioned wavelength determination conditions can be modified suitably for the wavelengths of the special illumination light.

First Modification of Third Embodiment

A first modification of the third embodiment is described. Here, the differences between the first modification and the third embodiment are described, and the same parts are provided with the same reference signs and are not described. An overview of a configuration example of the light source imaging apparatus 100 according to the present modification is shown in FIG. 14. In the example shown in the third embodiment, the normal illumination light emitted from the first to fourth semiconductor laser light sources and the special illumination light emitted from the eighth semiconductor laser light source 128 are emitted from the same light emitting portion 190. In contrast, in the present modification, as shown in FIG. 14, the normal illumination light are emitted from a first light emitting portion 190-1, and the special illumination light is emitted from a second light emitting portion 190-2.

In the present modification, the special observation light is one narrow-band light, so that the eighth semiconductor laser light source 128 and the second light emitting portion 190-2 are directly connected by one optical fiber 165 without any optical combiner in between, as shown in FIG. 14. When the special observation light includes more than one narrow-band light, the semiconductor laser light sources may be mixed by an optical combiner provided in addition to the optical combiner section 150 for the normal illumination light, and then guided to the second light emitting portion 190-2.

When the light source imaging apparatus 100 is configured as in the present modification, the configuration of the light emitting portion can be designed suitably for the purpose of an observation. For example, between the normal illumination light and the special observation light, the divergence angle can be varied suitably for purposes, or the degree of diffusion can be varied based on coherency, so that optimum designs can be provided for the normal illumination light and the special observation light, respectively.

Second Modification of Third Embodiment

Figure 15:
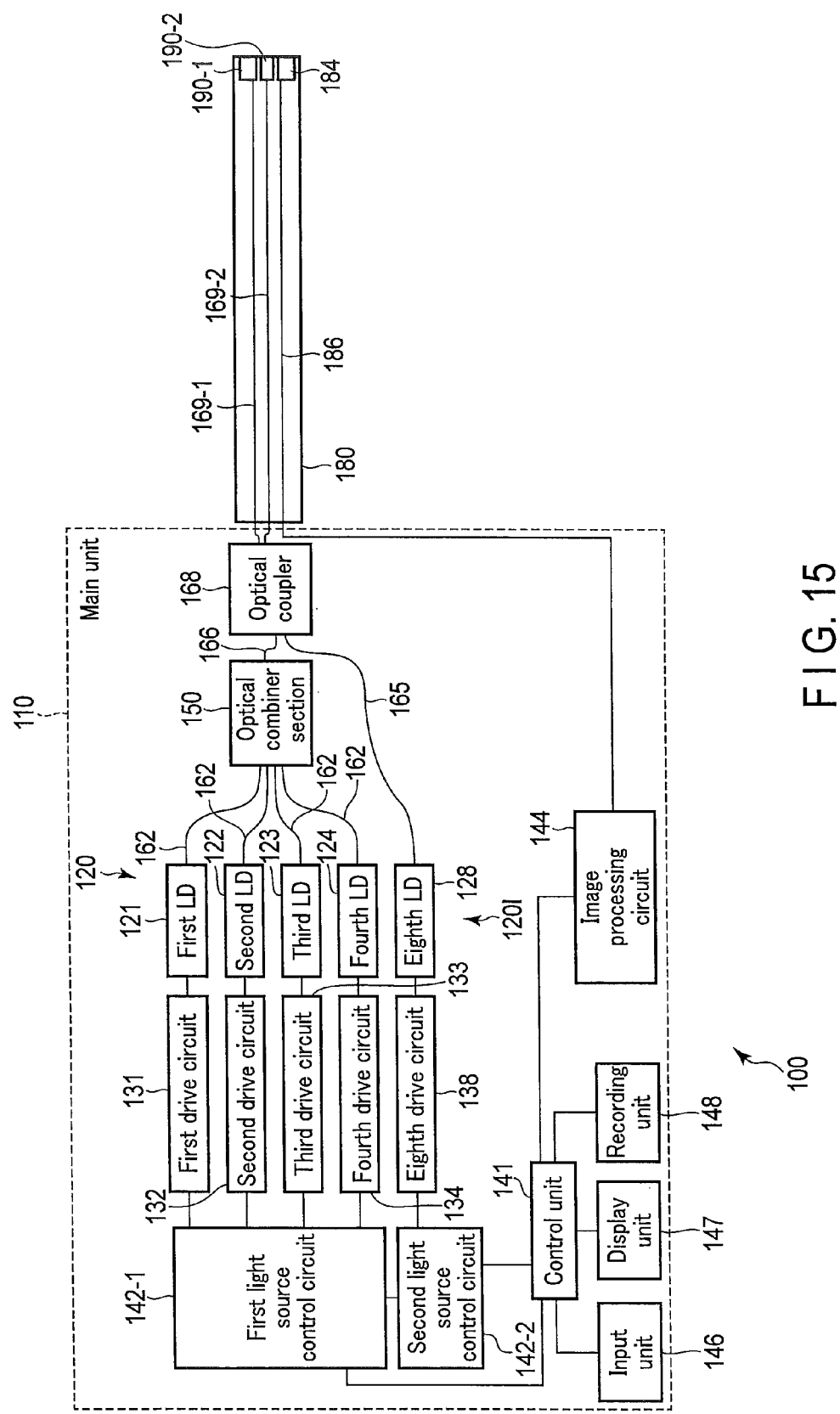
FIG. 15 is a block diagram showing an overview of a configuration example of a light source imaging apparatus according to a second modification of the third embodiment.

A second modification of the third embodiment is described. Here, the differences between the second modification and the third embodiment are described, and the same parts are provided with the same reference signs and are not described. A configuration example of the light source imaging apparatus 100 according to the present modification is shown in FIG. 15. As shown in this drawing, the basic configuration of the light source imaging apparatus 100 is similar to that in the first modification of the third embodiment described with reference to FIG. 14. The difference between the present modification and the first modification is that an optical coupler 168 is provided in the vicinity of a connection portion of the main unit 110 to the insertion portion 180. The optical coupler 168 is a 2-in-2-out optical coupler having two entrance ends and two exit ends. The optical coupler 168 has a function to divide, by a preset dividing ratio, the light that has entered from one of the two entrance ends, and emit the light from the two exit ends. In the present modification, this dividing ratio is 50:50, and the optical coupler has a function to divide a narrow-band light that has entered from one of the two entrance ends at an equal light intensity ratio, and then emit the light from the two exit ends. One of the two entrance ends of the optical coupler 168 is optically connected, through the exit side optical fiber 166, to the exit end of the 4-in-1-out optical combiner section 150 which mixes the narrow-band light emitted from the first to fourth semiconductor laser light sources. The other of the entrance ends of the optical coupler 168 is optically connected, through the optical fiber 165, to the exit end of the eighth semiconductor laser light source 128.

In the present modification, the narrow-band light emitted from the first to fourth semiconductor laser light sources mixed by the optical combiner section 150 are divided by the optical coupler 168 at a ratio of 50:50 and then emitted from the two exit ends of the optical coupler 168. The narrow-band light emitted from the eighth semiconductor laser light source 128 is also divided by the optical coupler 168 at a ratio of 50:50 and then emitted from the two exit ends of the optical coupler 168. A first optical fiber 169-1 and a second optical fiber 169-2 are connected to the two exit ends of the optical coupler, respectively. The first light emitting portion 190-1 is connected to the first optical fiber 169-1, and the second light emitting portion 190-2 is connected to the second optical fiber 169-2. Therefore, when the first to fourth semiconductor laser light sources are turned on, normal illumination light substantially equal in spectrum and light intensity is emitted from the first light emitting portion 190-1 and the second light emitting portion 190-2 via the optical combiner section 150, the optical coupler 168, and the first and second optical fibers. Similarly, when the eighth semiconductor laser light source 128 is turned on, special illumination light substantially equal in spectrum and light intensity is emitted from the first light emitting portion 190-1 and the second light emitting portion 190-2 via the optical coupler 168 and the first and second optical fibers.

When the light source imaging apparatus 100 is configured as in the present modification, normal illumination light and special illumination light substantially equal in spectrum and light intensity can be emitted from the two light emitting portions provided at the distal end of the insertion portion 180, the light intensity ratio between the normal illumination light and the special illumination light can be properly controlled, and the normal illumination light and the special illumination light can be freely emitted both simultaneously and singly. When the first light emitting portion 190-1 and the second light emitting portion 190-2 are properly arranged, for example, across the imaging unit 184, it is possible to provide a light source device which facilitates the observation of, for example, an uneven observation target without much shading.

Fourth Embodiment

A fourth embodiment is described. Here, the differences between the first embodiment and the fourth embodiment are described, and the same parts are provided with the same reference signs and are not described. The configuration of the light source imaging apparatus 100 according to the present embodiment is similar to the configuration of the light source imaging apparatus 100 according to the first embodiment described with reference to FIG. 1. The present embodiment is different from the first to third embodiments in the method of determining a combination of the wavelengths of the laser light emitted from the first to fourth semiconductor laser light sources.

In the first to third embodiments, the wavelengths of the laser light emitted from the light sources are determined by the peak wavelengths $\lambda nb$ of the narrow-band light to improve color reproducibility. In contrast, in the present embodiment, the wavelengths of the laser light emitted from the light sources are determined by a light emitting region. The light emitting region is a predetermined wavelength range, and at least one narrow-band light having the peak wavelength $\lambda nb$ is included in this range. More than one narrow-band light may be included in a certain light emitting region, in which case the wavelength gap between two kinds of narrow-band light is not particularly limited, and any wavelength gap can be set.

In the present embodiment, there are three kinds of light detection elements for the light receiving elements of the imaging unit 184, so that the number of light receiving regions K (K is a natural number) is 4. Each light receiving region includes one peak wavelength $\lambda nb$ of the narrow-band light. That is, as shown in FIG. 16, four light emitting regions are a first light emitting region in the B light sensitivity region except for the G light sensitivity region, a second light emitting region in the G light sensitivity region except for the R light sensitivity region, a third light emitting region in which the G light sensitivity region and the R light sensitivity region overlap, and a fourth light emitting region in the R light sensitivity region except for the G light sensitivity region. The light emitting regions do not overlap one another. Thus, the light emitting regions are determined by the light sensitivity characteristics of the image sensor used together.

A first light emitting region includes a blue laser light having a peak wavelength $\lambda nb=450$ nm, a second light emitting region includes a blue-green laser light having a peak wavelength $\lambda nb=520$ nm, a third light emitting region includes an orange laser light having a peak wavelength $\lambda nb=590$ nm, and a fourth light emitting region includes a red laser light having a peak wavelength $\lambda nb=650$ nm.

In the present embodiment, the B light wavelength sensitivity region includes the first light emitting region. The G light sensitivity region includes the second light emitting region and the third light emitting region. The R light sensitivity region includes the third light emitting region and the fourth light emitting region. That is, in the present embodiment, the G light detection element and the R light detection element are multiple light region detection elements including two or more light emitting regions. In contrast, the third light emitting region is included in the R light sensitivity region and the G light sensitivity region.

As described above, more light emitting regions which do not overlap one another than the number of kinds of light detection elements are arranged on the basis of the wavelength characteristics of the light detection elements of the imaging unit, resulting that color reproducibility can be higher than when the same number of light emitting regions as the kinds of light detection elements of the imaging unit are set.

Modification of Fourth Embodiment

A modification of the fourth embodiment is described. Here, the differences between the modification and the fourth embodiment are described, and the same parts are provided with the same reference signs and are not described. In the fourth embodiment, the light emitting regions are set only from the light sensitivity characteristics of the light detection elements of the imaging unit. In contrast, in the present modification, the light emitting regions are set in consideration of the spectral reflectance of the observation target in addition to the light sensitivity characteristics of the light detection elements.

As the spectral reflectance of the observation target, the test colors 8 and 15 that sharply change in spectral reflectance are considered among the test colors 1 to 8 used in the evaluation of a general color rendering index and the test color 15 based on the color of the skin of a Japanese person. As shown in FIG. 17, the wavelength of the test color 8 at which the spectral reflectance sharply changes is 590 nm, and the wavelength of the test color 15 at which the spectral reflectance sharply changes is 610 nm. Thus, based on the above, the wavelength $\lambda k$ at which the spectral reflectance sharply changes is set at 600 nm so that the light emitting regions are respectively set on the low reflectivity side and the high reflectivity side across this wavelength $\lambda k$. As a result of this setting, the general color rendering index can be improved.

That is, as in the fourth embodiment, the first light emitting region is a region in the B light sensitivity region except for the G light sensitivity region, the second light emitting region is a region in the G light sensitivity region except for the R light sensitivity region, and a fifth light emitting region ranges from 570 to 600 nm, and a sixth light emitting region ranges from 600 to 700 nm. Each of these light emitting regions includes the wavelength of at least one narrow-band light to be emitted. In this way, a light source having a high general color rendering index can be configured.

The sixth light emitting region of 600 to 700 nm may be a seventh light emitting region ranging from 625 to 700 nm as shown in FIG. 18. In these cases, the fifth light emitting region is included in both the R light sensitivity region and the G light sensitivity region. If the above-described modifications are further modified, it is possible to consider the color rendering properties of the image sensor and improve the general color rendering index.

Although the embodiments according to the present invention have only shown the examples of the use of the semiconductor laser light source or the compound semiconductor laser light source in which the semiconductor laser light source is combined with the SHG element as the light source to emit the narrow-band light, the present invention is not limited to this. That is, various solid-state lasers and gas lasers can be used. A superluminescent diode (SLD) and a light-emitting diode (LED) can also be used.

Although one light source emits only one narrow-band light in each of the embodiments shown by way of example, the present invention is not limited to this. It is possible to use a light source which simultaneously emits narrow-band light, such as an He—Cd laser light source which is a three-primary-color (white) laser light source for simultaneously oscillating a blue laser light of 441.6 nm, a green laser light of 537.8 nm, and a red laser light of 636.0 nm. In this case, the number of semiconductor laser light sources included in the light source imaging apparatus 100 shown in FIG. 1 and others is different from the number of narrow-band light emitted from the light source imaging apparatus 100.

Although the optical fiber according to each of the embodiments is a multimode single-wire optical fiber, the present invention is not limited to this. For example, a single-mode fiber can be used. Various optical fibers can also be used, such as a step-index or graded-index optical fiber, a plastic fiber, and a compound material type optical fiber having a plastic cladding and a glass core. It is also possible to use a bundle fiber in which the above optical fibers are bundled, and a general film-type or slab-type waveguide in which a waveguide is formed on a resin substrate or a semiconductor substrate by providing a refractive index distribution.

Although the light source imaging apparatus 100 including the light source device and the imaging device has been described by way of example in each of the above embodiments, the present invention is not limited to this. A light source device 101 shown in FIG. 19 which does not have the imaging unit 184 and its related configuration may be singly configured. This light source device may be used in an observation in combination with, for example, an imaging system and an image fiber that are not shown. The light source device may be used when a target is observed with the naked eye. That is, the light source device according to the present invention solves problems in manufacture such as the supply of the lasers and costs, and also provides high color reproducibility in the observation with the naked eye as well.

The embodiments are illustrative only, and various combinations and modifications can be made without departing from the spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source device to illuminate a target to be imaged by an imaging unit which comprises N (N is a natural number) kinds of light detection elements which wavelength sensitivity regions that are detectable wavelength bands are different each other, the light source device comprising:
   a light source configured to simultaneously emit different kinds of light which have different peak wavelengths, a difference between the peak wavelengths being equal to or more than an effective wavelength gap;
   an insertion portion configured to be inserted into an internal space of an object where the target exists;
   an illumination light emitting portion which is provided in the insertion portion and which emits an illumination light; and
   a light guide member which guides the light emitted from the light source to the illumination light emitting portion, the guided light being emitted from the illumination light emitting portion.

2. The light source device according to claim 1, wherein the light is narrow-band light and each of all the wavelength sensitivity regions comprises at least one of the peak wavelengths of the narrow-band light, and
   at least one of the wavelength sensitivity regions comprises two or more of the peak wavelengths.

3. The light source device according to claim 2, wherein
   when the wavelength sensitivity region comprising two or more of the peak wavelengths is referred to as a multiple light region, and
   when a wavelength region in which a change of a spectral reflectance of a test color is greater than a predetermined value is referred to as a sharp wavelength,
   the multiple light region comprises the peak wavelengths on a longer wavelength side and a shorter wavelength side than the sharp wavelength, respectively.

4. The light source device according to claim 2, wherein
   two or more of the peak wavelengths are included in a red wavelength sensitivity region which is the wavelength sensitivity region including a wavelength of 600 nm,
   at least one of the two or more peak wavelengths is within the red wavelength sensitivity region and is longer than 600 nm, and
   at least one of the two or more peak wavelengths is within the red wavelength sensitivity region and is shorter than 600 nm.

5. The light source device according to claim 2, wherein the wavelength sensitivity region comprises two or more of the peak wavelengths includes a wavelength region in which a spectral reflectance of the target is higher than a predetermined value and/or a wavelength region in which a change of the spectral reflectance of the target is higher than a predetermined value.

6. The light source device according to claim 1, wherein the light source is configured to emit M different kinds (M is a natural number greater than N) of narrow-band light which have different peak wavelengths.

7. The light source device according to claim 6, wherein M is between 4 and 100, inclusively.

8. The light source device according to claim 1, wherein the light source is configured to emit at least one further kind of light that has a different peak wavelength than each of the emitted different kinds of light, the at least one further kind of light having a peak wavelength within the effective wavelength gap.

9. The light source device according to claim 1, wherein the light is narrow-band light and the imaging unit comprises at least one pair of the light detection elements configured to have a sensitivity overlap region in which the wavelength sensitivity regions of different kinds of the light detection elements overlap, and
   at least one of the peak wavelengths of the narrow-band light is included in the sensitivity overlap region.

10. The light source device according to claim 1, wherein the N is 3, and
    the three kinds of light detection elements comprise
    a B light detection element configured to detect light within a blue wavelength sensitivity region;
    a G light detection element configured to detect light within a green wavelength sensitivity region; and
    an R light detection element configured to detect light within a red wavelength sensitivity region.

11. The light source device according to claim 10, wherein the light is narrow-band light and the red wavelength sensitivity region of the R light detection element comprises the peak wavelengths of two or more kinds of the narrow-band light.

12. The light source device according to claim 1, wherein the effective wavelength gap $\Delta\lambda$ satisfies $$V/(2(M+1)) \leq \Delta\lambda,$$

in which V is a width of the wavelength sensitivity region by all the light detection elements.

13. The light source device according to claim 1, wherein the effective wavelength gap $\Delta\lambda$ satisfies $$W/(2(q+1)) \leq \Delta\lambda$$

in which W is a width of the wavelength sensitivity region comprising q (q is a natural number of 2 or more) peak wavelengths.

14. The light source device according to claim 1, wherein the light is narrow-band light and the wavelengths of M kinds of narrow-band light are a combination of wavelengths which produce a white light when the M kinds of narrow-band light are mixed.

15. The light source device according to claim 1, wherein the light source comprises at least one of a semiconductor laser light source, superluminescent diode, a light-emitting diode and a compound semiconductor laser light source in which a semiconductor laser light source is combined with an optical element.

16. The light source device according to claim 1, wherein the light source comprises light source units, and
    further comprises a light source control circuit which controls some of the light source units independently of each other.

17. The light source device according to claim 1, further comprising:
    wherein the light is narrow-band light and an independent light source which emits an independent narrow-band light having a predetermined wavelength regardless of the wavelength of the narrow-band light emitted by the light source.

18. The light source device according to claim 17, wherein the independent narrow-band light is emitted from the illumination light emitting portion via the light guide member.

19. The light source device according to claim 17, further comprising:
    an independent light guide member which guides the independent narrow-band light to a distal end of the insertion portion; and an independent illumination light emitting portion which is provided at the distal end and which emits the independent narrow-band light guided by the independent light guide member.

20. A light source device to illuminate a target to be imaged by an imaging unit which comprises N (N is a natural number) kinds of light detection elements which wavelength sensitivity regions that are detectable wavelength bands are different each other, the light source device comprising:
   a light source which has K (K is a natural number greater than N) light emitting regions having different wavelength ranges and which simultaneously emits a plurality of kinds of light so that a peak wavelength of at least one kind of light is included in each of the light emitting regions;
   an insertion portion configured to be inserted into an internal space of an object where the target exists;
   an illumination light emitting portion which is provided in the insertion portion and which emits an illumination light; and
   a light guide member which guides the light emitted from the light source to the illumination light emitting portion, the guided light being emitted from the illumination light emitting portion.

21. The light source device according to claim 20, wherein
   each of all the wavelength sensitivity regions comprises at least one of the light emitting regions, and
   at least one of the wavelength sensitivity regions comprises two or more of the light emitting regions.

22. The light source device according to claim 20, wherein
   the imaging unit comprises at least one pair of the light detection elements configured to have a sensitivity overlap region in which the wavelength sensitivity regions of different kinds of the light detection elements overlap, and
   at least one of the light emitting regions is included in the sensitivity overlap region.

23. The light source device according to claim 20, wherein
   the N is 3, and
   the three kinds of light detection elements comprise
   a B light detection element configured to detect light within a blue wavelength sensitivity region;
   a G light detection element configured to detect light within a green wavelength sensitivity region; and
   an R light detection element configured to detect light within a red wavelength sensitivity region.

24. The light source device according to claim 20, wherein the K light is narrow-band light and the light source comprises at least one of a semiconductor laser light source, superluminescent diode, a light-emitting diode and a compound semiconductor laser light source in which a semiconductor laser light source is combined with an optical element.

25. A light source device to illuminate a target to be imaged by an imaging unit which comprises N (N is a natural number) kinds of light detection elements which wavelength sensitivity regions that are detectable wavelength bands are different each other, the light source device comprising:
   a light source which has K (K is a natural number greater than N) light emitting regions having different wavelength ranges and which emits a plurality of kinds of light so that a peak wavelength of at least one kind of light is included in each of the light emitting regions;
   an insertion portion configured to be inserted into an internal space of an object where the target exists;
   an illumination light emitting portion which is provided in the insertion portion and which emits an illumination light; and
   a light guide member which guides the light emitted from the light source to the illumination light emitting portion, the guided light being emitted from the illumination light emitting portion, wherein
   each of all the wavelength sensitivity regions comprises at least one of the light emitting regions, and
   at least one of the wavelength sensitivity regions comprises two or more of the light emitting regions
wherein
   when the wavelength sensitivity region comprises two or more of the light emitting regions is referred to as a multiple light region, and
   when a wavelength region in which a change of a spectral reflectance of a test color is greater than a predetermined value is referred to as a sharp wavelength,
   the multiple light region comprises the light emitting regions on a longer wavelength side and a shorter wavelength side than the sharp wavelength, respectively.

26. A light source device to illuminate a target to be imaged by an imaging unit which comprises N (N is a natural number) kinds of light detection elements which wavelength sensitivity regions that are detectable wavelength bands are different each other, the light source device comprising:
   a light source configured to emit M different kinds of light which have different peak wavelengths, a difference between the peak wavelengths being equal to or more than an effective wavelength gap;
   an insertion portion configured to be inserted into an internal space of an object where the target exists;
   an illumination light emitting portion which is provided in the insertion portion and which emits an illumination light; and
   a light guide member which guides the light emitted from the light source to the illumination light emitting portion, the guided light being emitted from the illumination light emitting portion,
wherein
   the N is 3, and
   the three kinds of light detection elements comprise
   a B light detection element configured to detect light within a blue wavelength sensitivity region;
   a G light detection element configured to detect light within a green wavelength sensitivity region; and
   an R light detection element configured to detect light within a red wavelength sensitivity region, and wherein
   the light is narrow-band light and the imaging unit is configured to comprise
   a first sensitivity overlap region in which the blue wavelength sensitivity region and the green wavelength sensitivity region overlap, and
   a second sensitivity overlap region in which the green wavelength sensitivity region and the red wavelength sensitivity region overlap,
   when a region in the blue wavelength sensitivity region except for the first sensitivity overlap region is referred to as a first light sensitivity region, when a region in the green wavelength sensitivity region except for the second sensitivity overlap region is referred to as a second light sensitivity region, when the second sensitivity overlap region is referred to as a third light sensitivity region, and when a region in the red wavelength sensitivity region except for the second sensitivity overlap region is referred to as a fourth light sensitivity region, the M is 4, and when the peak wavelengths of the four kinds of narrow-band light are referred to as a first peak wavelength, a second peak wavelength, a third peak wavelength, and a fourth peak wavelength in order from a short wavelength side to a long wavelength side, the first peak wavelength is included in the first light sensitivity region, the second peak wavelength is included in the second light sensitivity region, the third peak wavelength is included in the third light sensitivity region, and the fourth peak wavelength is included in the fourth light sensitivity region.

27. The light source device according to claim 26, wherein the effective wavelength gap is 40 nm, and differences between the first peak wavelength, the second peak wavelength, the third peak wavelength, and the fourth peak wavelength are equal to or more than the effective wavelength gap.

28. The light source device according to claim 26, wherein the blue wavelength sensitivity region is a region of 400 to 525 nm, the green wavelength sensitivity region is a region of 470 to 625 nm, and the red wavelength sensitivity region is a region of 570 to 700 nm.

29. The light source device according to claim 26, wherein the light source is configured to emit M different kinds (M is a natural number greater than N) of narrow-band light which have different peak wavelengths.

30. The light source device according to claim 29, wherein M is between 4 and 100, inclusively.

31. The light source device according to claim 29, wherein the light source is configured to emit at least one further kind of light that has a different peak wavelength than each of the M different kinds of narrow-band light, the at least one further kind of light having a peak wavelength within the effective wavelength gap.

32. A light source device to illuminate a target to be imaged by an imaging unit which comprises N (N is a natural number) kinds of light detection elements which wavelength sensitivity regions that are detectable wavelength bands are different each other, the light source device comprising:

a light source which has K (K is a natural number greater than N) light emitting regions having different wavelength ranges and which emits a plurality of kinds of light so that a peak wavelength of at least one kind of light is included in each of the light emitting regions;

an insertion portion configured to be inserted into an internal space of an object where the target exists;

an illumination light emitting portion which is provided in the insertion portion and which emits an illumination light; and a light guide member which guides the light emitted from the light source to the illumination light emitting portion, the guided light being emitted from the illumination light emitting portion, wherein the N is 3, and the three kinds of light detection elements comprise a B light detection element configured to detect light within a blue wavelength sensitivity region;

a G light detection element configured to detect light within a green wavelength sensitivity region; and an R light detection element configured to detect light within a red wavelength sensitivity region wherein the K is 4, and when the four light emitting regions are referred to as a first light emitting region, a second light emitting region, a third light emitting region, and a fourth light emitting region in order from a short wavelength side to a long wavelength side, the first light emitting region is included in the blue wavelength sensitivity region, the second light emitting region is included in the green wavelength sensitivity region, the third light emitting region is included in an overlap region in which the green wavelength sensitivity region and the red wavelength sensitivity region overlap, and the fourth light emitting region is included in a region in the red wavelength sensitivity region except for the overlap region.

33. The light source device according to claim 32, wherein the K light is narrow-band light and the light source comprises at least one of a semiconductor laser light source, superluminescent diode, a light-emitting diode and a compound semiconductor laser light source in which a semiconductor laser light source is combined with an optical element.

34. A light source device to illuminate a target to be imaged by an imaging unit which comprises N (N is a natural number) kinds of light detection elements which wavelength sensitivity regions that are detectable wavelength bands are different each other, the light source device comprising:

a light source configured to emit different kinds of light which have different peak wavelengths, a difference between the peak wavelengths being equal to or more than an effective wavelength gap, wherein the effective wavelength gap is 40 nm;

an insertion portion configured to be inserted into an internal space of an object where the target exists;

an illumination light emitting portion which is provided in the insertion portion and which emits an illumination light; and a light guide member which guides the light emitted from the light source to the illumination light emitting portion, the guided light being emitted from the illumination light emitting portion.

35. The light source device according to claim 34, wherein the light is narrow-band light and each of all the wavelength sensitivity regions comprises at least one of the peak wavelengths of the narrow-band light, and at least one of the wavelength sensitivity regions comprises two or more of the peak wavelengths.

36. The light source device according to claim 34, wherein the light is narrow-band light and the imaging unit comprises at least one pair of the light detection elements configured to have a sensitivity overlap region in which the wavelength sensitivity regions of different kinds of the light detection elements overlap, and at least one of the peak wavelengths of the narrow-band light is included in the sensitivity overlap region.

37. The light source device according to claim 34, wherein the N is 3, and the three kinds of light detection elements comprise a B light detection element configured to detect light within a blue wavelength sensitivity region;

a G light detection element configured to detect light within a green wavelength sensitivity region; and an R light detection element configured to detect light within a red wavelength sensitivity region.

38. The light source device according to claim 37, wherein the light is narrow-band light and the red wavelength sensitivity region of the R light detection element comprises the peak wavelengths of two or more kinds of the narrow-band light.

* * * * *